United States Patent [19]
Emerson et al.

[11] Patent Number: 5,681,735
[45] Date of Patent: Oct. 28, 1997

[54] TRANSCRIPTION CONTROL ELEMENT FOR INCREASING GENE EXPRESSION IN MYOBLASTS

[75] Inventors: Charles P. Emerson, Rydal; David J. Goldhamer, Philadelphia, both of Pa.

[73] Assignee: Fox Chase Cancer Center, Philadelphia, Pa.

[21] Appl. No.: 313,181
[22] PCT Filed: Mar. 24, 1993
[86] PCT No.: PCT/US93/02767
§ 371 Date: Oct. 7, 1994
§ 102(e) Date: Oct. 7, 1994
[87] PCT Pub. No.: WO93/21347
PCT Pub. Date: Oct. 28, 1993

Related U.S. Application Data

[63] Continuation of Ser. No. 866,386, Apr. 10, 1992, abandoned.
[51] Int. Cl.$^6$ .................. C07H 21/04; C12N 15/63; C12N 1/00; C12N 5/00
[52] U.S. Cl. .................. 435/240.2; 435/320.1; 536/24.1; 536/24.3
[58] Field of Search .................. 435/172.3, 320.1, 435/240.1, 243; 536/22.1, 23.1, 24.1, 24.3; 935/22, 23, 27, 34

[56] References Cited

U.S. PATENT DOCUMENTS 5,352,595 10/1994 Tapscott et al. .................. 435/172.3

OTHER PUBLICATIONS

Thompson et al. (1991) J. Biol. Chem. 266:22678–22688.
Jaynes et al. (1988) Mol. Cell. Biol. 8:62–70.
Pearson–White (1991) Nucleic Acids Res. 19:1148.
Zingg et al. (1991) Nucleic Acids Res. 19:6433–6439.
Barr et al. (1991) Science 254:1507–1509.
Dhawan et al. (1991) Science 254:1509–1512.
De la Brousse et al. (1990) Genes Dev. 4:567–581.
Pownall et al. (1992) Dev. Biol. 151:67–79.

*Primary Examiner*—David Guzo
*Assistant Examiner*—Robert Schwartzman
*Attorney, Agent, or Firm*—Dann, Dorfman, Herrell and Skillman, P.C.

[57] ABSTRACT

A transcription control element is provided for controlling gene expression in myogenic cells. The transcription control element comprises an isolated DNA segment having an enhancer activity in cultured cells and in non-cultured myogenic cells. The transcription control element is isolated from upstream regions of genes encoding bHLH myogenic regulatory proteins. Specifically, an enhancer element from the upstream region of human myoD and an enhancer element from the upstream region of a quail qmf1 are provided. These myoblast-specific transcription control elements are capable of significantly increasing the levels of gene expression in myogenic cells and are intended to be applied in gene therapy, using myoblast transfer and microinjection techniques, wherein myoblast-specific gene expression is desired or required.

17 Claims, 5 Drawing Sheets

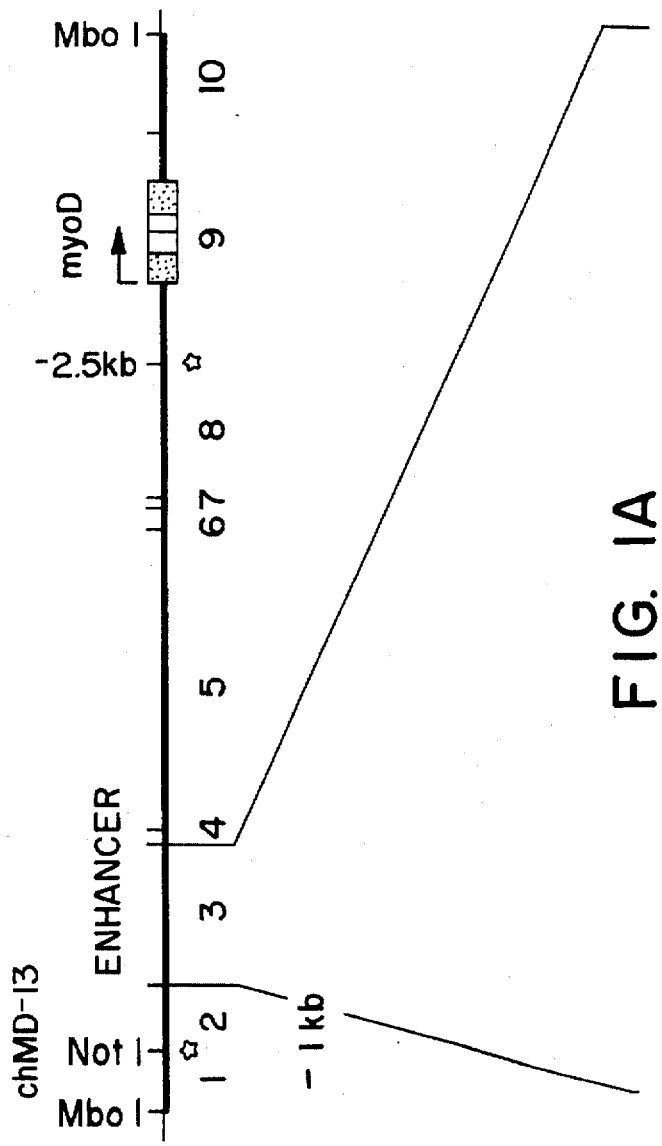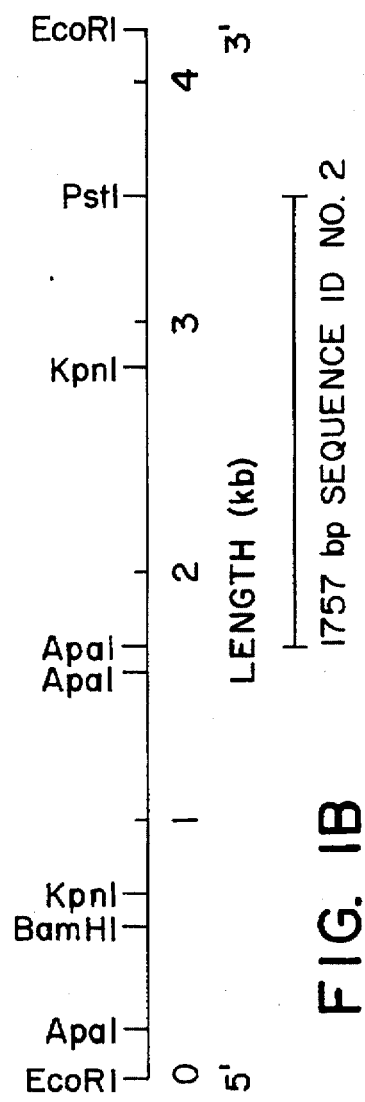
FIG. 1A
FIG. 1B 5,681,735

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 4086 base pairs
      ( B ) TYPE: nucleic acid
      ( C ) STRANDEDNESS: double
      ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:1:

```
ACAGACTCCA  CAAATCACAC  AGTTGGAAAC  TCTGAGTCTG  CACTCAACTG  GTCTGCAAAC      60

CGCACTCTCG  GAGACTTCAG  GTGAGATGAG  GTCAGGTTCT  CAGGCCAGGT  CCTGAAGTTT     120

GACACCTTGG  CGAAATGCAC  TTTCCTTGAC  TCAGCACCGC  GAGTGAGGCG  GAGCCAAGCC     180

CCGAGCAGAA  GGGTTTTCTT  CCCAGCTGAA  GAGGCAGCTC  AGCCTAGACC  CCAGGCATGG     240
```

| | | | | | |
|---|---|---|---|---|---|
| CACTGGACAC | CCCTGCTGTG | GAAACGTGCA | GATTTAGATG | GAGGGGATTC | CTAACCTGGG | 300 |
| CAGGATCCGA | GTTTGGAGAG | ATTGGCGCGA | ACGTTAGCA | GCAATCTCCG | ATTCCTGTAC | 360 |
| AACCATAGCT | GGGTTTCTAA | GCGTCTAGGG | AAGAAGGACT | GGGCCCACGA | CCTGCTGAGC | 420 |
| AACTCCCAGG | TCGGGGACTG | GCGGAATATC | AGAGCCTCTA | CGACCCGTTT | GTCTCGGGCT | 480 |
| CGCCCACTTC | AACTCTCGGG | GTCTCTCCGC | CTGTTGTTGC | ACTCGTGCGT | TTCTCTGCCC | 540 |
| CTGACGCTCT | AAGCTTTCTG | CTTTCTGCGT | GTCTCTCAGC | CTCTTTCGGT | CCCTCTTTCA | 600 |
| CGGTCTCACT | CCTCAGCTCT | GTGCCCCAA | TGCCTTGCCT | CTCTCCAAAT | CTCTCACGAC | 660 |
| CTGATTTCTA | CAGCCGCTCT | ACCCATGGGT | CCCCCACAAA | TCAGGGGACA | GAGGAGTATT | 720 |
| GAAAGTCAGC | TCAGAGGTGA | GCGCGCGCAC | AGCGTTTCCC | GCGGATACAG | CAGTCGGGTG | 780 |
| TTGGAGAGGT | TTGGAAAGGG | CGTGCCGGAG | AGCCAAGTGC | AGCCGCCTAG | GGCTGCCGGT | 840 |
| CGCTCCCTCC | CTCCCTGCCC | GGTAGGGGAC | CTAGCGCGCA | CGCCAGTGTG | GAGGGGCGGG | 900 |
| CTGGCTGGCC | AGTCTGCGGG | CCCTGCGGC | CACCCCGGGG | ACCCCCCCA | AGCCCGCCC | 960 |
| CGCAGTGTTC | CTATTGGCCT | CGGACTCCCC | CTCCCCAGC | TGCCCGCCTG | GGCTCCGGGG | 1020 |
| CGTTTAGGCT | ACTACGGATA | AATAGCCCAG | GGCGCCTGGC | GAGAAGCTAG | GGGTGAGGAA | 1080 |
| GCCCTGGGGC | TGCCGCCGCT | TTCCTTAACC | ACAAATCAGG | CCGGACAGGA | GAGGGAGGGG | 1140 |
| TGGGGACAGT | GGGTGGGCAT | TCAGACTGCC | AGCACTTTGC | TATCTACAGC | CGGGGCTCCC | 1200 |
| GAGCGGCAGA | AAGTTCCGGC | CACTCTCTGC | CGCTTGGGTT | GGCGAAGCCA | GGACCGTGCC | 1260 |
| GCGCCACCGC | CAGGATATGG | AGCTACTGTC | GCCAACCGCT | CCGCGACGTA | GACTGACGGC | 1320 |
| CCCCGACGGC | TCTCTCTGCT | CCTTTGCCAC | AACGGACGAC | TTCTATGACG | ACCCGTGTTT | 1380 |
| CGACTCCCCG | GACCTGCGCT | TCTTCGAAGA | CCTGGACCCG | CGCCTGATGC | ACGTGGGCGC | 1440 |
| GCTCCTGAAA | CCCGAAGAGC | ACTCGCACTT | CCCCGCGGCG | GTGCACCCGG | CCCCGGGCGC | 1500 |
| ACGTGAGGAC | GAGCATGTGC | GCGCGCCCAG | CGGGCACCAC | CAGGCGGGCC | GCTGCCTACT | 1560 |
| GTGCCTGCAA | GGCGTGCAAG | CGCAAGACCA | CCAACGCCGA | CCGCCGCAAG | GCCGCCACCA | 1620 |
| TGCGCGAGCG | GCGCCGCCTG | AGCAAAGTAA | ATGAGGCCTT | TGAGACACTC | AAGCGCTGCA | 1680 |
| CGTCGAGCAA | TCCAAACCAG | CGGTTGCCCA | AGGTGGAGAT | CCTGCGCAAC | GCCATCCGCT | 1740 |
| ATATCGAGGG | CCTGCAGGCT | CTGCTGCGCG | ACCAGGACGC | GCGCCCCTG | GCGCCGCAGC | 1800 |
| CGGCCTTCTA | TGCGCCGGGC | CCGCTGCCCC | GGGCCGCGG | CGGCGAGCAC | TACAGCGGCG | 1860 |
| ACTCCGACGC | GTCCAGCCCG | CGCTCCAACT | GCTCCGACGG | CATGGTAAGG | CCGGGACCCC | 1920 |
| AGGAAGTGAG | GAAGTTAGGG | CGGCGCTCGG | GATATCAGGG | ACGCGTTTCC | GAGGGCGGGG | 1980 |
| AGCTGGCCTT | GCGGGAGGTT | TGGGCCAGGA | TCCTTCCCGA | GAGAGGAC | CCCCTTGTCC | 2040 |
| TGGGCAGCTG | TCACTGGGGT | AGCCTGTTTT | GGAAGTGTGC | GGGCAAGCGT | TCGAGCTGCC | 2100 |
| CCATTGGGGG | CGCTATTAGA | ACACTGCAGC | GCGAACGTGA | AGATCTTTTT | CTCTACTTAT | 2160 |
| CCCTACTTCC | AAAATGTAAA | TTTGCGCCCC | TTGGTGACTG | TCCGCCCTTG | GTTTGGCCCT | 2220 |
| GCATGTTGCA | GACCTCATCT | CCTACCCACC | CGTAATTACC | CCCCAACCA | GGACAGGTCT | 2280 |
| GGGCCCGGAA | CTAGAGCCTT | AGGCTAGAGT | TAGGGAGGGG | GCGGCTACAG | GAATTGGTGT | 2340 |
| TCGGGCCTCG | AGCCGTCCCG | CGGGCCTGAC | TCAGTCGCCC | TTCTGTTTGC | AGATGGACTA | 2400 |
| CAGCGGCCCC | CCGAGCGGCG | CCCGGCGGCG | GAACTGCTAC | GAAGGCGCCT | ACTACAACGA | 2460 |
| GGCGCCCAGC | GGTGGGTATT | CCGGGCCTCT | CCCTGCTCGC | TCCTCCTCCT | TCATGGAGCT | 2520 |
| GTCCTGGCCT | CTATCTAGGA | CGCTCCCACC | CCCACTCACA | CACGCCTATG | TCCTGGGAAG | 2580 |
| TGGTGCAGGA | GATGAAATAC | TAAGCAAGTA | GCTCCCTGTC | TTTTCGATTG | TCCCGGACTC | 2640 |

-continued

| | | | | | |
|---|---|---|---|---|---|
| TAACTAAAGT | CCTCAGTTTC | CAATCTGTCT | CAAAGTACTG | GGCCCGGGGG | TGGGAGGCTT | 2700 |
| GTCGCGGCCC | CACCCCTGCT | TACTAACCGA | GCCCTCCCCG | CGCAGAACCC | AGGCCCGGGA | 2760 |
| AGAGTGCGGC | GGTGTCGAGC | CTAGACTGCC | TGTCCAGCAT | CGTGGAGCGC | ATCTCCACCG | 2820 |
| AGAGCCTGCG | GCGCCCGCCC | TCCTGCTGGC | GGACGTGCCT | TCTGAGTCGC | CTCCGCGCAG | 2880 |
| GCAAGAGGCT | GCCGCCCCCA | GCGAGGGAGA | GAGCAGCGGC | GACCCCACCC | AGTCACCGGA | 2940 |
| CGCCGCCCCG | CAGTGCCCTG | CGGGTGCGAA | CCCCAACCCG | ATATACCAGG | TGCTCTGAGG | 3000 |
| GGATGGTGGC | CGCCCACCCC | AACCCCGCCC | GAGGGATGGT | GCCCTAGGG | TCCCTCGCGC | 3060 |
| CCAAAAGATT | GAACTTAAAT | GCCCCCCTCC | CAACAGCGCT | TTAAAAGCGA | CCTCTCTTGA | 3120 |
| GGTAGGAGAG | GCGGGAGAAC | TGAAGTTTCC | GCCCCGCCC | CACAGGGCAA | GGACACAGCG | 3180 |
| CGGTTTTTTC | CACGCAGCAC | CCTTCTCGGA | GACCCATTGC | GATGGCCGCT | CCGTGTTCCT | 3240 |
| CGGTGGGCCA | GAGCTGAACC | TTGAGGGGCT | AGGTTCAGCT | TTCTCGCGCC | CTCCCCATGG | 3300 |
| GGGTGAGACC | CTCGCAGACC | TAAGCCCTGC | CCCGGGATGC | ACCGGTTATT | GGGGGGGCG | 3360 |
| TGAGACCCAG | TGCACTCCGG | TCCCAAATGT | AGCAGGTGTA | ACCGTAACCC | ACCCCAACC | 3420 |
| CGTTCCCGG | TTCAGGACCA | CTTTTGTAA | TACTTTGTA | ATCTATTCCT | GTAAATAAGA | 3480 |
| GTTGCTTTGC | CAGAGCAGGA | GCCCCTGGGG | CTGTATTTAT | CTCTGAGGCA | TGGTGTGTGG | 3540 |
| TGCTACAGGG | AATTTGTACG | TTTATACCGC | AGGCGGGCGA | GCCGCGGGCG | CTCGCTCAGG | 3600 |
| TGATCAAAAT | AAAGGCGCTA | ATTTATACCG | CCGTGGCTCC | GGCTTTCCCT | GGACATGGGT | 3660 |
| GTGGGATCCG | GAGGAAAATC | CGCAAACTGG | GCCAGCTGTC | CCTCAGCGAC | GCCTGTAGGC | 3720 |
| GGCAGGCGGA | TTGCAAGGAG | GAAGCCTGCT | GCCTGGGAA | GGAAGGAGGG | GTGCAAATTT | 3780 |
| CTCCAGTACG | TGAGGAAGTT | CCTCTGACCT | TGACTACATT | ACTACACACG | TCCGTGGCTC | 3840 |
| TTATGGAAGG | GTACACAGGT | TGATATGAGT | ATTTTTAAA | CCCATGTCTG | AGCTCGCCCC | 3900 |
| CTAGATATTC | TGATTTAATG | TTTCTGCCCC | ATATACCCAG | GGCCAGGTAT | TGGTATTTTT | 3960 |
| TTTCAAAAGC | TCCCCAAGTG | ATTCTGAAGT | TCATTCAAGG | CTGAGAATCA | TCCCTCCATA | 4020 |
| TAAGTGAGTG | AACCCAGGTG | TGATACAGAG | ACACGGAGTG | TGCCAGGCAT | CACTTGGGGC | 4080 |
| TCGTGG | | | | | | 4086 |

(2) INFORMATION FOR SEQ ID NO:2:

(i) SEQUENCE CHARACTERISTICS:
        (A) LENGTH: 1757 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:2:

| | | | | | |
|---|---|---|---|---|---|
| CCACAGCAGT | TGGGGGCATT | TATGGGCCTT | CCTATAAACT | TCTGAGAGGG | TAACTTTATC | 60 |
| CTGCTTCTTT | CAGCCAAGTA | TCCTCCTCCA | GCAGCTGGTC | ACAAAGCTGG | TTAATCTCCC | 120 |
| AGAGTGCTCA | GCTTAAAACC | CGTGACTCAC | AGCACAGCCA | GTGTGGGGA | GGGGTGGCT | 180 |
| GCCTCCAATA | CGTGGCGCCC | AGAGTCAGCT | GTTCTGGGGC | CTTCTCTGGT | TTCTCCAACT | 240 |
| GAGTCCTGAG | GTTTGGGGCC | TTGTCTTCCT | TCCTGGAGTC | CTGCTTCTCA | CTGACCCCTA | 300 |

| | | | | | | |
|---|---|---|---|---|---|---|
|CATACAAGCC|ATGAGAGGTC|AGGGACCTGA|GAGGAGGGCC|AGTTCCAGGC|CTTGGCTTTG|360|
|GCCAAGCCCT|CAGGCTATCC|CAGAAATGAC|CAGAAGGCCT|TGGCCTTCCA|GAGAAGGGGA|420|
|AGGTTTCAAG|TGTAACTCTG|GGAGGGGTTG|GTCCTGAAAT|TGGGGTCCCT|GCCTCACCTG|480|
|CCCAGACCTG|GAAAAATTCC|CTTCAGCCAT|GACCCTCTCA|TGGCGGATCT|TCATTCCCTG|540|
|TCAGCATGTG|ACATGAAACC|TGTGTATGGT|GGCTGAAGTG|AGCTAGCAAA|AAGTAACACA|600|
|AATGACAGGG|GACCTCTGAC|TTGAGATCAG|CAGAATAAAC|ACAAGTCGAG|TCAGGTAGAA|660|
|AAGGTGGAGT|AGTGTTTTGG|CCTTGGAGAG|ACATGGGTTC|AAGTCCCAAC|TCTGCCACCT|720|
|ACTAGCTGAA|TAGCTTCCCT|GAGCCTCTGT|TTCCTCCTCT|GTAAACTGG|GATAGTAATA|780|
|GCATTACCTT|GGCGAGCTAA|TGTGAGAATC|AAAACCTATT|TTCCTGCTTA|GTAGGTGGGA|840|
|GCTATTAATA|TTATTGTTGT|TATCGTCATC|ATCATACTGC|TCAAAAAGCA|GGAGAATCCA|900|
|TTTTCATTTG|TCAGGGGACT|TATGTTTGTA|TAGCGGGGAG|GGAAGCTAAT|GGTCTGAAAG|960|
|GATTTCAGTG|ACACCTCTCA|CTTGGCAGGA|AATCTATTCT|GATGAATATG|ACTCTGTAAA|1020|
|TGATAAGGGA|GTATCTGCCA|GCCAGTGGCA|TCGTGCTTGT|TATGGTTGAA|GACCTAACCC|1080|
|AGGAAACAGC|TATAGCAGAT|ACACGACGGA|GGCTCCCACT|GGTACCTCTA|CTGAGCAAAG|1140|
|CACAAATCGT|GTGCTAACCC|TTGCTCCTGT|GGTGCCAGTG|ATTCTCAATA|CCTTCTACTC|1200|
|CATCTGAAAA|GTCCATACT|CATCCAAAGA|TTCCTGTGTG|TAAGGAGGAA|TGAACCACTT|1260|
|TATAAGTTCC|TGTTATGGGC|CAGACACTAT|ATTAAACACA|AATATTTGAC|CATATCTAAC|1320|
|CCTTACAACA|TCCCTTGGAG|TGGGTATACT|ATTATCTACA|TGTGGTGGAC|CAATTATATT|1380|
|AATGAATCTA|GTTCTTCACT|CCTCCTCGTA|TTCATACCCT|TTGCCTTATG|ATTTTGCAAC|1440|
|TCTTCATATC|AGGAGGCATA|TTGTGTATTT|CTCCATGTCT|CAGTTCTGAG|TTCAGCCATG|1500|
|TAACTTGTTT|TAACCCATGA|GATATTAACA|TATATGAATC|AGGCAGAGGT|TTGGGAAATG|1560|
|TGCTTATGTT|TCTGCTTGCA|CTTTTGCACC|ACTACCATTA|CCATGAAAAC|ACGCCTAGGC|1620|
|TAGCCTGCTA|GAGGTGAGGC|CTGTGGAGCG|CAGCTGAGTC|GCCCAGTTCC|CCAGCCAAGA|1680|
|CCAGCCTGAG|CCAGTAAAGT|ACAGCATGTG|AGTGAGCCCA|GCAGAGCCTA|GGAAAACAGA|1740|
|CCAATCTAAA|TAGCCAA| | | | |1757|

( 2 ) INFORMATION FOR SEQ ID NO:3:

( i ) SEQUENCE CHARACTERISTICS:
        ( A ) LENGTH: 2235 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Quail (Coturnix spp.)

( x i ) SEQUENCE DESCRIPTION: SEQ ID NO:3:

| | | | | | | |
|---|---|---|---|---|---|---|
|ACGTTGTCAA|GGAAAATTCT|GAGTCTTTTT|TAAAAGTGAA|AGCCAACACA|GTAGCACTGA|60|
|CACTTGTGTG|TATTTGTGGT|GAGGTCAATG|ACTGTTATGG|ATTTTAGACT|GTTTTTTTTC|120|
|TGCCTGTGCC|ATTCTGGCTA|CCACCTCTGC|TCCTTGAAGT|GACTCTGCTT|TGCTTCTTTC|180|
|TGTAATATAT|CCCATCTGGA|CATGGTCCAA|GTGGAAAGTG|ACTCAAAACT|AATCAAACCT|240|
|CAGAAGGTCA|AAANTGAAAA|GAGGTACAGT|TCAGGGAAAT|ACATGTTAGA|ATACGTGTTA|300|

-continued

```
GAGAAGTTGT GACTGGTGAT ATGAGCAGCT TGTAGCAAGG TCATGTTTTC CCCTAACACT    360
GCTTTGTGAG CACTTTGGAA AGCCTACTTT TGCTCAGGTT TTGTCTGATG TGTCCCAGAA    420
CGGGATCATC CATATTTCCT TGAAGGATGC TTATGGTCTA GAATCTGGGA TGCAAACAGG    480
ACTGAGGGAC ACATCTTGTG AGGCAGCAGT AAGGCCATGG TACGTGGGCA GAGGGAGGGT    540
AGTGAAGTTT GCCATGTGTA GCTTTTGACT TGTAGCTGTN TGCTTTGAAG CAGGAGACAA    600
GAAGATTTAT TTTCCTTTTT GAAGGAAGAT CAGTGCACAG CAAAGATAGG TGAGAAGTTC    660
CAAGGAAAAC TAAACAGAGA AGAAGCAG CACTAACTGG CAGAGTGGGC CAAACCTTTC    720
ACTGTTGTAT ATGGGCATTA CTCATACAAC TTCAAGAGAG TACATGATTG AACTGAGCAT    780
GTACCAGCTG AGGGCCTGGC CCATAATGTT CNTTATAAAG GTCCGATTCC TCCCCAAATA    840
GTTTTTCCCT CTCTCTTCAA AGGGGCACCT GTTGTTGGAG GAGCTGGTGA TGATACTGGA    900
TTAGTGCACA TGCGGTCAGC CCACTTGGCC TCGGCCCTTT GGACCCAAAA TGAACTCCAG    960
CTGCTGTTAC CCAGAGCAGG TGCTTCATCC AGCCTGTGCA GCTGTTTGAA TGCATGCTGT   1020
TGTGGCCAAT AGGCGGGGTG AGTCCTCTGA ACTACCAGGG GAAGAGCTGG TCAGCAGGAG   1080
GGAAGGGAAA GGCACAGAGC TGGGTTTCTT ATACCCAGCA TTTAGCAAGG AGACAGTGTT   1140
CCAGCATAGT ATGGTGGAAA TGGGAAACAG TGGCTGGTAT CCTGCATGCA ACATGCCCAC   1200
ATGACCCAGT GATGGATGCT TGTTCCCAAA ATGAGGCTGA GACCTATAGA ATACCAGCAG   1260
GACCCTGACA AATGCTGGAT CTGTAAGATG CTGAATCTCC CTTGTCAGTT ACTGGCCTAG   1320
TGTGAGACAT TCAGAGGGCT GCTGGCATCT AACAGTTACT CAGTGTTTTC AGCCACTGGT   1380
TTAAAGCTTT AAAGAGCTGC CTGGCGAAGG TGAGATAGGC GCAGAGCGCG TGCAGGGTGA   1440
ATATCTGTGA CGTGCAANAG CTGAAACCAG CAGCAAGGA AGATGACAAA AGCAGAGGGA   1500
AATGGGTTAA GATGCAGCCA CGGGAGTGCA AGGGACTGTG CCAGGTCAGT GGAGGGTGAG   1560
GAGACNCGGG CGTTCAGAGT TAGGGAAGGC TGGAAGTCAG CAGCCAGAGT TTGAAGAAGG   1620
AGTATAGACA GGTAACACCA ATGGTAGAGC AGTGGTAACC CAGGGAGGGN NAGAGAGAAG   1680
GGAGCAGGGC AGGNNTGAAG GTTTCTTTTT TCTACATTGC ATATGGTTTC AGTCAGGTCT   1740
CATCAGCCAG GCTTCTCATT CTTCATGCCT TTGCTAATTG CTCAAGCAAG CTCTCAGCGA   1800
ACCTCCATAT TTCATTTTTC ATTACAGTGT GGCGCAAGCC CAGGAGAAAA ACATAAATAT   1860
TTGAGGCCTC TCTTTGTCAG GAAATGGGAT TTCNGCAGGT GCTCATTTGC AAATACTGTG   1920
CATGCTTCTG AGGCTTGGNA TANGGCATTG CTAAATCCTG ATTCAGGATG CAAGAATGTC   1980
TCGTGGCCTC TGCCATGTAA ACTGTTGTCC GCCCAAGTTT GGAAGTCAGC CCTCAGTGAT   2040
GGCACTAGAC AAGTATGGGT GAAATGAGCA GCTTGGCTTC AGCACTGAGC AAGACTTGTT   2100
AAACACTGTA AGTACAGATG GGCCAATTCA CAGTTTGAAT AGTATAACAA TACATATATA   2160
TATAATATTA TGGCTTTTTC TGCAGGNNNT CGANNNNANN NNNNNCGATA CCGACGACCT   2220
CGAGGGGGGC CGGTA                                                   2235
```

1

TRANSCRIPTION CONTROL ELEMENT FOR INCREASING GENE EXPRESSION IN MYOBLASTS

This application is a 371 of PCT/US93/02767, filed Mar. 24, 1993, which is a continuation of 07/866,386, filed Apr. 10, 1992, now abandoned.

Pursuant to 35 U.S.C. §202(c), it is hereby acknowledged that the U.S. Government has certain rights in the invention described herein, which was made in part with funds from the National Institutes of Health.

FIELD OF THE INVENTION

The present invention relates to the field of gene expression and gene therapy. Specifically, a transcription control element is provided for controlling gene expression in myogenic cells.

BACKGROUND

Vertebrate skeletal muscle fibers are formed by the cellular fusion of progenitor myoblasts, which are embryonic cells that proliferate and populate the muscle-forming regions of embryos. Myogenic lineages become determined during somite morphogenesis, leading to the formation of stably determined myoblasts.

The process of myoblast differentiation into muscle fibers has been investigated in cell cultures of clonal embryonic myoblasts and established myoblast cell lines. In dispersed cell cultures, myoblasts can proliferate clonally in the presence of medium rich in growth factors, but retain their potential to differentiate in fused muscle fibers. Thus, myoblasts are a stably determined cell type, capable of extensive cell division, the progeny of which faithfully inherit their myoblast identity and can express their potential to differentiate into muscle fibers. The growth and differentiation of myoblasts is controlled by extracellular factors, specifically growth factors such as basic fibroblast growth factor (bFGF) and transforming growth factor-β (TGF-β). In the presence of such growth factors, myoblasts proliferate, whereas in reduced concentrations of such factors, myoblasts can exist in the cell cycle in $G_1$, fuse and differentiate into contractile fibers.

Myogenesis, therefore, involves "determination" of the myoblast lineages in the somite and "differentiation" of myofibers in the muscle-forming regions of the embryo. The molecular mechanisms regulating cell lineage determination have been studied using the mouse cell line C3H10T1/2 (10T1/2). Konieczny and Emerson, Cell, 38: 791 (1984). This model cell culture system has allowed identification of several mammalian genes (myoD, myogenin, Myf-5 and MRF-4) that regulate the determination of the skeletal lineage. These genes encode transcription factors comprising a subgroup within the basic helix-loop-helix (bHLH) superfamily of Myc-related DNA binding proteins.

It has been determined that the bHLH myogenic regulatory proteins are evolutionarily conserved, as evidenced by amino sequence homology. Pownall et al., Seminars in Devel. Biol., 3: 229–241 (1992); de la Brousse et al., Genes and Devel. 4: 567–581 (1990). Specifically, it has been shown that the protein qmf1, a myoD protein from quail (QMyoD) shares extensive homology with mouse MyoD1, Myf5, myogenin and a MyoD1 sequence from *Xenopus Laevis* (XMyoD). de la Brousse et al., supra.

As transfected cDNAs, the aforementioned myogenic regulatory factors induce myogenic conversion of multipotential 10T1/2 cells to stably determined populations of proliferative myogenic cells. Consistent with their function in determination, these myogenic regulatory genes are expressed exclusively in skeletal muscle lineages of the embryo, beginning at the early stages of somite formation. Although these transcription factors regulate the determination of skeletal muscle lineage, they themselves are also regulated. The transcriptional regulatory mechanisms that activate their expression in the skeletal muscle lineage of the embryo have heretofore remained unknown.

Because myoblasts are proliferative (i.e., regenerative) and are capable of fusing together to form mature muscle fibers when injected into already-developed muscle tissue, the technique of myoblast transfer has been proposed as a potential therapy or cure for muscular diseases. Myoblast transfer involves injecting myoblast cells into the muscle of a patient requiring treatment. Although developed muscle fibers are not regenerative, the myoblasts are capable of a limited amount of proliferation, thus increasing the number of muscle cells at the location of myoblast infusion. Myoblasts so transferred into mature muscle tissue will proliferate and differentiate into mature muscle fibers. This process involves the fusion of these mononucleated myogenic cells (myoblasts) to form a multinucleated syncytium (myofiber or myotube). Thus, muscle tissue which has been compromised either by disease or trauma may be supplemented by the transfer of myogenic progenitor cells, i.e., myoblasts, into the compromised tissue.

Myoblast transfer may also be used in gene therapy, a utility enhanced by the ability of myoblasts to proliferate and fuse. Potentially, myoblasts could be genetically altered by one of several means to comprise functional genes which may be defective or lacking in a patient requiring such therapy. The recombinant myoblast can then be transferred to a patient, wherein they will multiply and fuse and, additionally, express recombinant genes. Using this technique, a missing or defective gene in a patient's muscular system may be supplemented or replaced by infusion of genetically altered myoblasts.

It has been shown that myoblasts injected into genetically deficient mdx mice fuse into the muscle fibers of the host, and are capable of expressing a recombinant gene product, dystrophin (an intracellular protein, the lack of which causes Duchenne muscular dystrophy (DMD)). Partridge et al., Nature, 337: 176 (1989); Morgan et al., J. Cell. Biol., 111: 2437 (1990); Karpati et al., Am. J. Pathol., 135: 27 (1989). In a recent study involving human patients, normal myoblasts from fathers or unaffected siblings have been transplanted into the muscles of several boys afflicted with DMD, resulting in expression of normal donor dystrophin in the injected muscle tissue. Gussoni et al., Nature, 356: 435–438 (1992). Long-term expression of a non-muscle gene product (human growth hormone) has also been achieved using myoblast transfer of genetically engineering myoblasts into mouse muscle. Dhawan et al., Science, 254: 1509–12 (1991). Therefore, gene therapy using myoblast transfer may be applied in providing essential gene products not only to muscle tissue, but through secretion from muscle tissue to the bloodstream as well.

Although gene therapy via myoblast transfer has great potential utility, that utility is limited by the fact that, currently, there are no myoblast-specific promoters or enhancers available to induce gene expression in recombinant myoblasts. Such transcription control elements are needed for myoblast-mediated gene therapy for two reasons: (1) to enable useful genes (e.g., genes involved in autocrine regulation of myoblast development) to be expressed in myoblasts; and (2) to restrict such recombinant gene expression to myoblasts and their progeny. Thus, to facilitate myoblast-mediated gene therapy, myoblast-specific transcription control elements are needed.

Myoblast-specific enhancers of gene expression could also provide a much-needed alternative to artificial manipulation of muscle mass in agricultural animals. Currently, muscle weight in food animals, such as cows, pigs and chickens, is manipulated by traditional breeding programs and by hormone treatment, e.g., growth hormone. Hormone treatment of animals to facilitate weight gain is expensive, leading to an increased market price of the animal, as well as presenting potential dangers to consumers who may be sensitive to such food additives. Clearly, if weight gain could be mediated by an alternative means, the potentially hazardous use of hormone treatment could be obviated.

The availability of techniques for creating transgenic animals by introducing inheritable genetic alterations at the embryo stage offers a potential vehicle for manipulating muscular development by genetic engineering. However, specific manipulation of progenitor embryo cells of myogenic lineage requires the availability of myogenic lineage-specific promoters and enhancers. Otherwise, muscle-specific genetic alterations could not be introduced. The availability of such enhancers is necessary for the development of genetically-based improvements in muscle size and growth, heretofore achievable only through more time-consuming or otherwise undesirable techniques, such as hormone treatment.

SUMMARY OF THE INVENTION

In accordance with the present invention, transcription control elements that regulate gene expression in myogenic cells are provided. According to one aspect of the invention, there is provided an isolated DNA segment having an enhancer activity in cultured cells and in non-cultured, myogenic cells. This enhancer activity causes increased expression of a target gene when the DNA segment and the target gene are disposed within a DNA strand and the DNA segment is so position in the 5' direction relative to the target gene to permit the increased expression of that target gene. In a preferred embodiment, the isolated DNA segment having enhancer activity is isolated from a 50–100-kb region adjacent in the 5' direction to a gene encoding a bHLH myogenic regulatory protein.

According to another aspect of the present invention, there is provided a DNA segment isolated and purified from an approximately 25.5-kb fragment adjacent in the 5' direction to a human myoD gene, having a nucleotide sequence substantially the same as Sequence I.D. No. 2, described herein. In a preferred embodiment, there is provided a DNA segment consisting essentially of a nucleotide sequence substantially the same as bases 1–258 of Sequence I.D. No. 2, described herein. There is also provided a DNA segment isolated and purified from an approximately 18-kb fragment adjacent in the 5' direction to a quail qmf1 gene, having a nucleotide sequence substantially the same as Sequence I.D. No. 3, described herein.

According to another aspect of the present invention, vectors are provided which comprise the DNA segments described above. Additionally, procaryotic or eucaryotic host cells transformed or transfected with such vectors are also provided.

According to another aspect of the present invention, there are provided antisense oligonucleotides having sequences capable of hybridizing with a DNA segment having the above-described enhancer activity. Such antisense oligonucleotides will be useful for identifying and locating particularly functional regions in the transcription control elements of the invention.

According to another aspect of the present invention, there is provided an isolated DNA segment having an enhancer activity in cultured cells, which may be isolated by a method comprising: (1) obtaining test segments of DNA sequences from the 5' upstream region within 100-kb of a gene encoding a bHLH myogenic regulatory protein, which are suspected of having such enhancer activity; (2) preparing a set of test constructs, each one containing one of the test segments, a reporter gene and a vector adapted for expression in a cultured eucaryotic cell, the test segment and the reporter gene being so located relative to each other and to any regulatory sequences of the vector to permit expression of the reporter gene, as well as the enhancing activity, if present, of the test segment; (3) similarly preparing a control construct comprising a reporter gene and the vector, but not having a test segment; (4) introducing the test constructs or the control constructs into cultured eucaryotic cells under conditions permitting the expression of the reporter gene (the expression of the reporter gene causes formation of a detectable product, which is formed in an amount correlatable to expression of the gene); (5) comparing the amount of detectable product formed from the test construct with the amount of detectable product formed in cells having the control construct, the magnitude of the ratio between the two being indicative of enhancer activity suspected of being possessed by the test segment; and (6) identifying and isolating each test segment found to possess such enhancer activity.

According to yet another aspect of the present invention, there is provided an isolated DNA segment having enhancer activity specifically in myogenic cells of a living animal, which is isolated by a method comprising: (1) obtaining test segments of DNA sequences from the 5' upstream region within 100-kb of a gene encoding a bHLH myogenic regulatory protein, which are suspected of having such enhancer activity; (2) preparing a set of test constructs, each test construct comprising a test segment and a reporter gene, as well as any regulatory sequences necessary for expression of the reporter gene in cells of a vertebrate embryo, all sequences being so located relative to each other to permit expression of the reporter gene, as well as the enhancing activity, if present, of the test segment; (3) introducing the test constructs or the control constructs into cultured eucaryotic cells under conditions permitting the expression of the reporter gene (the expression of the reporter gene causes formation of a detectable product, which is formed in an amount correlatable to expression of the gene); (4) determining which, if any, cells of the vertebrate embryo form the detectable product, the formation of detectable product specifically in myogenic cells being indicative of enhancer activity; and (5) identifying and isolating the test segments possessing such enhancer activity.

The myoblast-specific transcription control elements of the present invention will enable significant advances in the field of gene therapy using myoblast transfer and microinjection techniques. Currently, genetic manipulations using these techniques are performed with recombinant genes under the control of promoters and enhancers that are not specificto myogenic cells. Such lack of myoblast specificity limits the utility of these methods for gene therapy, or other genetic engineering techniques, which requires that genes be expressed only in myogenic cell lineages, or during the course of muscle development. The transcription control elements of the present invention provide the requisite myoblast specificity.

Another advantageous application of a myoblast-specific transcription control element of the invention relates to the observation that, because an enhancer such as the myoD enhancer, is turned "on" and "off", it must itself be regulated by trancription factors operating very early in myogenic lineage determination. The transcription control element of the invention could be utilized to great advantage in biochemical assays for activity of such early transcription factors.

BRIEF DESCRIPTION OF THE DRAWINGS

FIG. 1A is a map of human cosmid clone chMD-13. EcoR1 (unmarked vertical lines) and NotI restriction sites, and presumed Mbo1 cloning sites are indicated. Exons and introns in MyoD are shown by solid and open blocks, respectively. For reference, restriction fragments for enzymes shown are labelled sequentially from the 5' to the 3' end of the cosmid cloning vector. Thick line, human sequences (to scale); thin line, pWE15 vector sequence. Numerals 1–10 beneath the thick line refer to EcoR1 fragments comprising chMD-13.

FIG. 1B is a map of EcoR1 Fragment 3 of cosmid clone chMD-13. Apa1, BamH1, Kpn1 and Pst1 restriction sites are shown. Numerals 0–4 beneath the horizontal line refer to length in kilobases. The location of a 1757 bp region of chMD-13 Fragment 3, corresponding to Sequence I.D. No. 2 is indicated.

DETAILED DESCRIPTION

Figure 2:
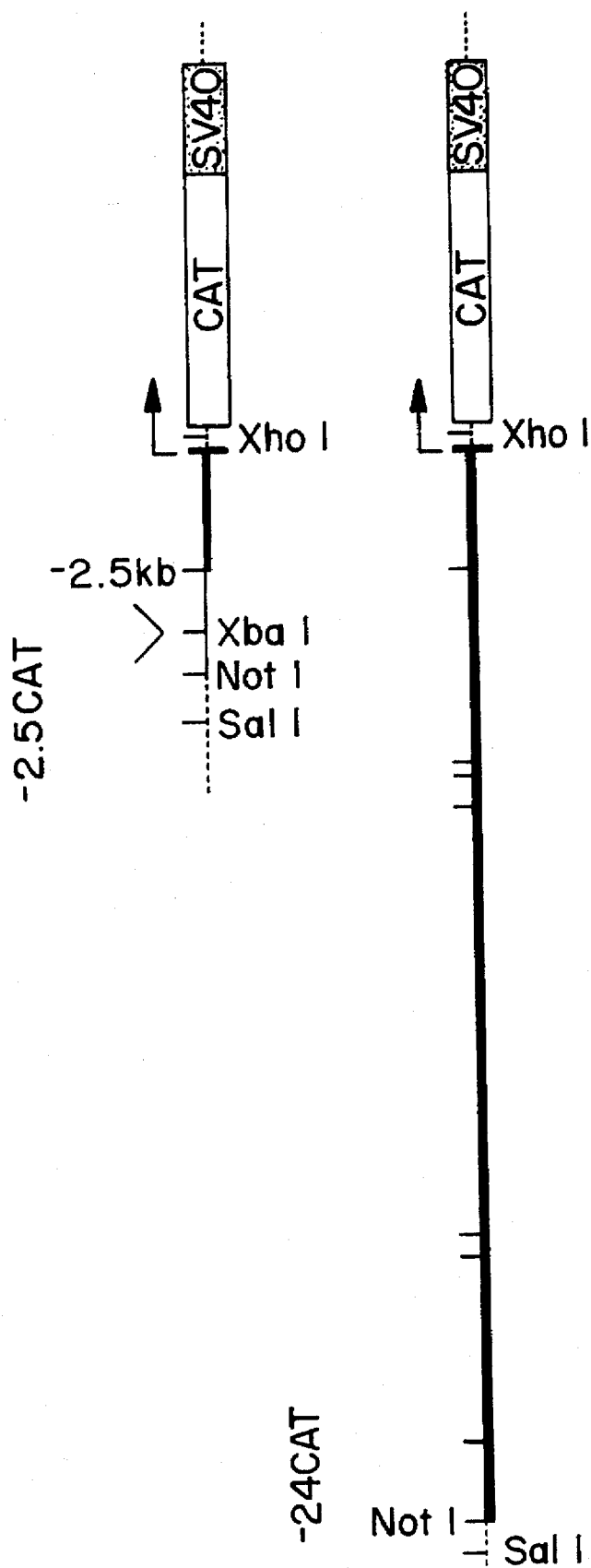
FIG. 2 illustrates CAT constructs comprising upstream myoD transcription control elements. EcoR1 restriction sites (unmarked vertical lines) are indicated. –2.5CAT and –24CAT refer to CAT reporter gene constructs with the minimal and maximal amounts of human myoD upstream sequences appended to the reporter gene. Thick line, human sequences (to scale); thin line, pBluescript vector sequence; dotted line, ptkCAT EH vector sequence. CAT structural gene sequences and SV40 sequences are indicated.

The following words and phrases are defined, for reference in describing the invention, as follows:

1. Transcription control element: refers to an isolated DNA segment that, under specified conditions, possesses a transcription-controlling activity with respect to expression of a target gene. An enhancer is a type of transcription control element. Enhancers generally increase the expression of a target gene when placed in appropriate proximity thereto. The term "transcription control element" and "enhancer" are used interchangeably herein when referring to the isolated DNA segments of the present invention.

2. Myogenic cell: refers to a stably determined cell type, capable of extensive cell division, the progeny of which faithfully inherit their myoblast identity and possess the potential for differentiating into mature muscle fibers. The terms "myoblast" and "myogenic cell" are used interchangeably herein.

3. Target gene: refers to a gene upon which a transcription control element of the invention exerts its transcription control activity. Specifically, an enhancer element of the invention, when placed upstream from the target gene causes increased expression of the target gene. As used herein, "target genes" contain promoters. These promoters can be the homologous promoter of the target gene or they can be a heterologous promoter. However, the target gene must be under the control of a promoter.

4. "Substantially the same as": when referring to specific DNA sequences set forth herein, "substantially the same as" means taking into account minor variations or substitutions that arise for a number of reasons, but do not alter the overall characteristics of the DNA molecule defined by the sequence. For example, homologous regions isolated from different strains or sub-species of an animal may possess sequence polymorphisms that render those sequences substantially the same as, but not identical to, the sequences set forth herein. Additionally, errors in analyzing DNA sequence information, or entering such information into a record system, may also produce sequences that are substantially the same, but not identical to, the sequences set forth herein.

5. "Approximately": when used herein in describing DNA fragment lengths or, "approximately" means within a margin of commonly acceptable error for the determination of DNA fragment size or relative position on a DNA strand by standard methods, such as agarose gel electrophoresis and comparison with standard fragments of known size.

In accordance with the present invention, it has now been discovered that expression of the human myoD gene is regulated not only by a promoter, but also by a distal enhancer sequence 18–22 kilobases upstream (5') from the myoD gene. Transcriptional activity of the myoD promoter and enhancer was assayed in myogenic cells derived from the multipotential 10T1/2 cell line by 5-azacytidine treatment. The myoD enhancer and promoter were active in myogenic and nonmyogenic cell lines. The myoD promoter itself was found to be only weakly active unless coupled with the upstream enhancer sequence. Moreover, the myoD enhancer sequence was also found to be capable of enhancing gene expression even when coupled with a heterologous promoter, e.g., the herpes virus thymidine kinase (HSVtk) promoter.

A second myoD enhancer (referred to herein as qmf1) encoding a quail MyoD protein (QMyoD), has also been isolated and cloned. Like the human myoD enhancer, the qmf1 enhancer is active in myogenic and non-myogenic cell lines. The qmf1 enhancer sequence can also enhance gene expression when coupled with either the qmf1 promoter, or a heterologous promoter, such as the herpes virus thymidine kinase (HSVtk) promoter. However, unlike the human myoD enhancer, the qmf1 enhancer is located approximately 11.5–15 kb upstream from the qmf1 gene. Moreover, the qmf1 enhancer contains no extensive sequence homology with the human myoD enhancer sequence.

It has further been found that, although the two myoD promoters and enhancers are active in non-myogenic cultured cells, in transgenic mouse embryos the human myoD enhancer and the qmf1 enhancer direct expression of genes specifically to the skeletal muscle lineage (myoblasts) only. However, the spatial and temporal expression of genes under the control of the human myoD enhancer is different from that of genes under the control of the qmf1enhancer, as described in greater detail in Example 6 below.

Insofar as is known, the above-described enhancers are the first myoblast-specific enhancers to be isolated and cloned. These enhancers may be utilized with a homologous or heterologous promoter to enhance myoblast-specific gene expression, as will be described in further detail below.

The description which follows sets forth the general procedures involved in practicing the present invention. To the extent that specific materials are mentioned, it is merely for purposes of illustration and is not intended to limit the invention.

I. Preparation of Myoblast-Specific Transcription Control Elements

Myoblast-specific transcription control elements may be prepared by two general methods: (1) they may be synthesized from appropriate nucleotide triphosphates, or (2) they may be isolated and purified from biological sources. Both methods utilize protocols that are known in the art. Unless otherwise specified, standard cloning and recombinant DNA procedures, such as those described in Sambrook et al., *Molecular Cloning*, Cold Spring, Harbor Laboratory (1989) (hereinafter "Sambrook et al.") are used.

Where DNA sequence information is known, a myoblast-specific enhancer of the invention may be prepared by oligonucleotide synthesis. Synthetic oligonucleotides may be prepared by the phosphoramadite method employed in the applied Biosystems 380A DNA Synthesizer or similar devices. The resultant construct may be purified according to procedures well known in the art, e.g., by high performance liquid chromatography (HPLC). Long, double-stranded polynucleotides, such as those of the present invention, will have to be synthesized in stages, due to the size limitations inherent in current oligonucleotide synthetic methods. Thus, for example, a 4-kb double-stranded DNA molecule may be synthesized as several smaller segments of appropriate complementarity. Complementary segments thus produced may be annealed such that each segment possesses appropriate cohesive termini for attachment of an adjacent segment. Adjacent segments may be ligated via annealing of cohesive termini in the presence of DNA ligase, to construct an entire 4-kb double-stranded molecule. A synthetic DNA molecule so constructed may then be cloned and amplified in an appropriate vector.

The constructs of the present invention may be maintained in any convenient cloning vector. In a preferred embodiment, large constructs are maintained in a cosmid cloning/transfer vector, such as pWE15 (Stratagene), which is propagated in a suitable *E. coli* host cell, e.g., *E. coli* strain NM554 (Stratagene), and which also may be transferred to mammalian cells. Alternatively, constructs may be maintained in lambda vectors (e.g., λEMBL), which are often used to construct genomic libraries. Smaller constructs are conveniently cloned into plasmids.

Myoblast-specific transcription control elements may be isolated from appropriate biological sources using methods known in the art. In one preferred embodiment, a human myoD transcription control element is isolated and cloned. A myoblast genomic library may be constructed in cosmid clones. The library can be screened with a cDNA, such as a full length mouse myoD cDNA as described by Pinney et al., Cell, 53: 781 (1988). Clones identified by such a screening may be analyzed, e.g., by restriction mapping, for the presence of significant amounts of upstream DNA sequence. Clones having up to 50 kb 5' to the myoD gene may be selected and analyzed for enhancer and promoter activity. Due to limitations in current technology, commonly-used cloning vectors cannot contain more than approximately 50 kb of inserted DNA. For this reason, the 5' region 50–100 kb from the myoD gene will have to be identified by a second screening step, using previously-identified clone containing upstream sequences 25–50 kb from the myoD gene. Such strategies for obtaining far distal sequences are commonly employed by those skilled in the art.

A cosmid clone comprising the human myoD gene and an approximately 25 kb upstream region, which constitutes a myoblast-specific transcription control element in accordance with the present invention, was constructed. A diagram of this construct is provided in FIG. 1A. The human myoD transcriptional control element comprises several distinctive features. A promoter region is present in the 2.5 kb fragment immediately 5' to the gene. The DNA sequence of the human myoD gene, including 1 kb of upstream sequence comprising the promoter region, is set forth below, as Sequence ID No. 1. The locations of the putative TATA box, the 3' end of the promoter region, and the translation start site of the myoD gene product are indicated.

```
  1 ACAGACTCCA CAAATCACAC AGTTGGAAAC TCTGAGTCTG CACTCAACTG

51 GTCTGCAAAC CGCACTCTCG GAGACTTCAG GTGAGATGAG GTCAGGTTCT

101 CAGGCCAGGT CCTGAAGTTT GACACCTTGG CGAAATGCAC TTTCCTTGAC

151 TCAGCACCGC GAGTGAGGCG GAGCCAAGCC CCGAGCAGAA GGGTTTTCTT

201 CCCAGCTGAA GAGGCAGCTC AGCCTAGACC CCAGGCATGG CACTGGACAC

251 CCCTGCTGTG GAAACGTGCA GATTTAGATG GAGGGGATTC CTAACCTGGG
```

-continued

```
 301 CAGGATCCGA GTTTGGAGAG ATTGGCGCGA ACGTTTAGCA GCAATCTCCG

351 ATTCCTGTAC AACCATAGCT GGGTTTCTAA GCGTCTAGGG AAGAAGGACT

401 GGGCCCACGA CCTGCTGAGC AACTCCCAGG TCGGGGACTG GCGGAATATC

451 AGAGCCTCTA CGACCCGTTT GTCTCGGGCT CGCCCACTTC AACTCTCGGG

501 GTCTCTCCGC CTGTTGTTGC ACTCGTGCGT TTCTCTGCCC CTGACGCTCT

551 AAGCTTTCTG CTTTCTGCGT GTCTCTCAGC CTCTTTCGGT CCCTCTTTCA

601 CGGTCTCACT CCTCAGCTCT GTGCCCCAA TGCCTTGCCT CTCTCCAAAT

651 CTCTCACGAC CTGATTTCTA CAGCCGCTCT ACCCATGGGT CCCCCACAAA

701 TCAGGGGACA GAGGAGTATT GAAAGTCAGC TCAGAGGTGA GCGCGCGCAC

751 AGCGTTTCCC GCGGATACAG CAGTCGGGTG TTGGAGAGGT TTGGAAAGGG

801 CGTGCCGGAG AGCCAAGTGC AGCCGCCTAG GGCTGCCGGT CGCTCCCTCC

851 CTCCCTGCCC GGTAGGGGAC CTAGCGCGCA CGCCAGTGTG GAGGGGCGGG

901 CTGGCTGGCC AGTCTGCGGG CCCCTGCGGC CACCCCGGGG ACCCCCCCCA

951 AGCCCCGCCC CGCAGTGTTC CTATTGGCCT CGGACTCCCC CTCCCCCAGC

1001 TGCCCGCCTG GGCTCCGGGG CGTTTAGGCT ACTACGGATA AATAGCCCAG
                                    *** ****(a)
1051 GGCGCCTGGC GAGAAGCTAG GGGTGAGGAA GCCCTGGGGC TGCCGCCGCT

1101 TTCCTTAACC ACAAATCAGG CCGGACAGGA GAGGGAGGGG TGGGGACAGT

1151 GGGTGGGCAT TCAGACTGCC AGCACTTTGC TATCTACAGC CGGGGCTCCC

1201 GAGCGGCAGA AAGTTCCGGC CACTCTCTGC CGCTTGGGTT GGCGAAGCCA
                                              ↑ (b)
1251 GGACCGTGCC GCGCCACCGC CAGGATATGG AGCTACTGTC GCCAACCGCT
                                               ***(c)
1301 CCGCGACGTA GACTGACGGC CCCCGACGGC TCTCTCTGCT CCTTTGCCAC

1351 AACGGACGAC TTCTATGACG ACCCGTGTTT CGACTCCCCG GACCTGCGCT

1401 TCTTCGAAGA CCTGGACCCG CGCCTGATGC ACGTGGGCGC GCTCCTGAAA

1451 CCCGAAGAGC ACTCGCACTT CCCCGCGGCG GTGCACCCGG CCCCGGGCGC

1501 ACGTGAGGAC GAGCATGTGC GCGCGCCCAG CGGGCACCAC CAGGCGGGCC

1551 GCTGCCTACT GTGCCTGCAA GGCGTGCAAG CGCAAGACCA CCAACGCCGA

1601 CCGCCGCAAG GCCGCCACCA TGCGCGAGCG GCGCCGCCTG AGCAAAGTAA

1651 ATGAGGCCTT TGAGACACTC AAGCGCTGCA CGTCGAGCAA TCCAAACCAG

1701 CGGTTGCCCA AGGTGGAGAT CCTGCGCAAC GCCATCCGCT ATATCGAGGG
```

-continued

```
1751 CCTGCAGGCT CTGCTGCGCG ACCAGGACGC GCGCCCCCTG GCGCCGCAGC

1801 CGGCCTTCTA TGCGCCGGGC CCGCTGCCCC CGGGCCGCGG CGGCGAGCAC

1851 TACAGCGGCG ACTCCGACGC GTCCAGCCCG CGCTCCAACT GCTCCGACGG

1901 CATGGTAAGG CCGGGACCCC AGGAAGTGAG GAAGTTAGGG CGGCGCTCGG

1951 GATATCAGGG ACGCGTTTCC GAGGGCGGGG AGCTGGCCTT GCGGGAGGTT

2001 TGGGCCAGGA TCCTTCCCGA GAGAGAGGAC CCCCTTGTCC TGGGCAGCTG

2051 TCACTGGGGT AGCCTGTTTT GGAAGTGTGC GGGCAAGCGT TCGAGCTGCC

201  CCATTGGGGG CGCTATTAGA ACACTGCAGC GCGAACGTGA AGATCTTTTT

2151 CTCTACTTAT CCCTACTTCC AAAATGTAAA TTTGCGCCCC TTGGTGACTG

2201 TCCGCCCTTG GTTTGGCCCT GCATGTTGCA GACCTCATCT CCTACCCACC

2251 CGTAATTACC CCCCAACCA GGACAGGTCT GGGCCCGGAA CTAGAGCCTT

2301 AGGCTAGAGT TAGGGAGGGG GCGGCTACAG GAATTGGTGT TCGGGCCTCG

2351 AGCCGTCCCG CGGGCCTGAC TCAGTCGCCC TTCTGTTTGC AGATGGACTA

2401 CAGCGGCCCC CCGAGCGGCG CCCGGCGGCG GAACTGCTAC GAAGGCGCCT

2451 ACTACAACGA GGCGCCCAGC GGTGGGTATT CCGGGCCTCT CCCTGCTCGC

2501 TCCTCCTCCT TCATGGAGCT GTCCTGGCCT CTATCTAGGA CGCTCCCACC

2551 CCCACTCACA CACGCCTATG TCCTGGGAAG TGGTGCAGGA GATGAAATAC

2601 TAAGCAAGTA GCTCCCTGTC TTTTCGATTG TCCCGGACTC TAACTAAAGT

2651 GTCGCGGCCC CACCCCTGCT TACTAACCGA GCCCTCCCCG CGCAGAACCC

2701 GTCGCGGCCC CACCCCTGCT TACTAACCGA GCCCTCCCCG CGCAGAACCC

2751 AGGCCCGGGA AGAGTGCGGC GGTGTCGAGC CTAGACTGCC TGTCCAGCAT

2801 CGTGGAGCGC ATCTCCACCG AGAGCCTGCG GCGCCCGCCC TCCTGCTGGC

2851 GGACGTGCCT TCTGAGTCGC CTCCGCGCAG GCAAGAGGCT GCCGCCCCCA

2901 GCGAGGGAGA GAGCAGCGGC GACCCCACCC AGTCACCGGA CGCCGCCCCG

2951 CAGTGCCCTG CGGGTGCGAA CCCCAACCCG ATATACCAGG TGCTCTGAGG

3001 GGATGGTGGC CGCCCACCCC AACCCCGCCC GAGGGATGGT GCCCCTAGGG

3051 TCCCTCGCGC CCAAAAGATT GAACTTAAAT GCCCCCCTCC CAACAGCGCT

3101 TTAAAAGCGA CCTCTCTTGA GGTAGGAGAG GCGGGAGAAC TGAAGTTTCC
```

-continued

```
3151 GCCCCCGCCC CACAGGGCAA GGACACAGCG CGGTTTTTTC CACGCAGCAC

3201 CCTTCTCGGA GACCCATTGC GATGGCCGCT CCGTGTTCCT CGGTGGGCCA

3251 GAGCTGAACC TTGAGGGGCT AGGTTCAGCT TTCTCGCGCC CTCCCCATGG

3301 GGGTGAGACC CTCGCAGACC TAATGCCCTGCCCGGGATGC ACCGGTTATT

3351 TGGGGGGGCG TGAGACCCAG TGCACTCCGG TCCCAAATGT AGCAGGTGTA

3401 ACCGTAACCC ACCCCCAACC CGTTTCCCGG TTCAGGACCA CTTTTTGTAA

3451 TACTTTTGTA ATCTATTCCT GTAAATAAGA GTTGCTTTGC CAGAGCAGGA

3501 GCCCCTGGGG CTGTATTTAT CTCTGAGGCA TGGTGTGTGG TGCTACAGGG

3551 AATTTGTACG TTTATACCGC AGGCGGGCGA GCCGCGGGCG CTCGCTCAGG

3601 TGATCAAAAT AAAAGGCGCTAATTTATACCG CCGTGGCTCC GGCTTTCCCT

3651 GGACATGGGT GTGGGATCCG GAGGAAAATC CGCAAACTGG GCCAGCTGTC

3701 CCTCAGCGAC GCCTGTAGGC GGCAGGCGGA TTGCAAGGAG GAAGCCTGCT

3751 GCCTGGGGAA GGAAGGAGGG GTGCAAATTT CTCCAGTACG TGAGGAAGTT

3801 CCTCTGACCT TGACTACATT ACTACACACG TCCGTGGCTC TTATGGAAGG

3851 GTACACAGGT TGATATGAGT ATTTTTTAAA CCCATGTCTG AGCTCGCCCC

3901 CTAGATATTC TGATTTAATG TTTCTGCCCC ATATACCCAG GGCCAGGTAT

3951 TGGTATTTTT TTTCAAAAGC TCCCCAAGTG ATTCTGAAGT TCATTCAAGG

4001 CTGAGAATCA TCCCTCCATA TAAGTGAGTG AACCCAGGTG TGATACAGAG

4051 ACACGGAGTC TGCCAGGCAT CACTTGGGGC TCGTGG
```

(a) - Putative TATA box
(b) - 3' end of promoter region
(c) - Translation start site An enhancer element is present in a 4 kb fragment approximately 18–22 kb upstream from the human myoD gene (Fragment 3). A restriction map of this fragment is shown in FIG. 1. The DNA sequence of approximately 1.7 kb of this fragment is set forth hereinbelow as Sequence ID No. 2.

```
  1 CCACAGCAGT TGGGGGCATT TATGGGCCTT CCTATAAACT TCTGAGAGGG

51 TAACTTTATC CTGCTTCTTT CAGCCAAGTA TCCTCCTCCA GCAGCTGGTC

101 ACAAAGCTGG TTAATCTCCC AGAGTGCTCA GCTTAAAACC CGTGACTCAC

151 AGCACAGCCA GTGTGGGGGA GGGGGTGGCT GCCTCCAATA CGTGGCGCCC

201 AGAGTCAGCT GTTCTGGGGC CTTCTCTGGT TTCTCCAACT GAGTCCTGAG

251 GTTTGGGGCC TTGTCTTCCT TCCTGGAGTC CTGCTTCTCA CTGACCCCTA
```

-continued

```
301 CATACAAGCC ATGAGAGGTC AGGGACCTGA GAGGAGGGCC AGTTCCAGGC

351 CTTGGCTTTG GCCAAGCCCT GAGGCTATCC CAGAAATGAC CAGAAGGCCT

401 TGGCCTTCCA GAGAAGGGGA AGGTTTCAAG TGTAACTCTG GGAGGGGTTG

451 GTCCTGAAAT TGGGGTCCCT GCCTCACCTG CCCAGACCTG GAAAAATTCC

501 CTTCAGCCAT GACCCTCTCA TGGCGGATCT TCATTCCCTG TCAGCATGTG

551 ACATGAAACC TGTGTATGGT GGCTGAAGTG AGCTAGCAAA AAGTAACACA

601 AATGACAGGG GACCTCTGAC TTGAGATCAG CAGAATAAAC ACAAGTCGAG

651 TCAGGTAGAA AAGGTGGAGT AGTGTTTTGG CCTTGGAGAG ACATGGGTTC

701 AAGTCCCAAC TCTGCCACCT ACTAGCTGAA TAGCTTCCCT GAGCCTCTGT

751 TTCCTCCTCT GTAAAACTGG GATAGTAATA GCATTACCT  GGCGAGCTAA

801 TGTGAGAATC AAAACCTATT TTCCTGCTTA GTAGGTGGGA GCTATTAATA

851 TTATTGTTGT TATCGTCATC ATCATACTGC TCAAAAAGCA GGAGAATCCA

901 TTTTCATTTG TCAGGGACT TATGTTTGTA TAGCGGGGAG GGAAGCTAAT

951 GGTCTGAAAG GATTTCAGTG ACACCTCTCA CTTGGCAGGA AATCTATTCT

1001 GATGAATATG ACTCTGTAAA TGATAAGGGA GTATCTGCCA GCCAGTGGCA

1051 TCGTGCTTGT TATGGTTGAA GACCTAACCC AGGAAACAGC TATAGCAGAT

1101 ACACGACGGA GGCTCCCACT GGTACCTCTA CTGAGCAAAG CACAAATCGT

1151 GTGCTAACCC TTGCTCCTGT GGTGCCAGTG ATTCTCAATA CCTTCTACTC

1201 CATCTGAAAA GTCCCATACT CATCCAAAGA TTCCTGTGTG TAAGGAGGAA

1251 TGAACCACTT TATAAGTTCC TGTTATGGGC CAGACACTAT ATTAAACACA

1301 AATATTTGAC CATATCTAAC CCTTACAACA TCCCTTGGAG TGGGTATACT

1351 ATTATCTACA TGTGGTGGAC CAATTATATT AATGAATCTA GTTCTTCACT

1401 CCTCCTCGTA TTCATACCCT TTGCCTTATG ATTTTGCAAC TCTTCATATC

1451 AGGAGGCATA TTGTGTATTT CTCCATGTCT CAGTTCTGAG TTCAGCCATG

1501 TAACTTGTTT TAACCCATGA GATATTAACA TATATGAATC AGGCAGAGGT

1551 TTGGGAAATG TGCTTATGTT TCTGCTTGCA CTTTTGCACC ACTACCATTA

1601 CCATGAAAAC ACGCCTAGGC TAGCCTGCTA GAGGTGAGGC CTGTGGAGCG

1651 CAGCTGAGTC GCCCAGTTCC CCAGCCAAGA CCAGCCTGAG CCAGTAAAGT
```

-continued

```
1701 ACAGCATGTG AGTGAGCCCA GCAGAGCCTA GGAAAACAGA CCAATCTAAA

1751 TAGCCAA
```

The two subregions of the sequenced portion of the enhancer element identified to date which have particular enhancing activity map to bp 1–258 and 1185–1757. The subregion mapping to bp 1–258 appears to confer myoblast specificity, while the 1185–1757 subregion affects the amount of expression-enhancing activity. It will be apparent to those skilled in the art that other regions, particularly 5' to the sequenced region may also have activity.

In another preferred embodiment, a quail myoD transcription control element is isolated and cloned. In this embodiment, a genomic library from quail embryonic primary myofibers is constructed in a lambda vector, and screening with a cDNA encoding a QMyoD regulatory protein, such as the quail qmf1 cDNA clone as described by de la Brousse et al., Genes and Devel., 4: 567–581 (1990).

Clones identified by the screening are analyzed for the presence of significant amounts of upstream DNA sequences, and clones having up to 50 kb 5' to the qmf1 are selected and analyzed for enhancer and promoter activity. DNA sequences farther upstream may also be analyzed by conducting a secondary screening as described above.

A λ EMBL3 clone comprising the qmf1 gene and approximately 18 kb upstream region, which constitutes a myoblast-specific transcription control element in accordance with the invention, was isolated. A diagram of this construct (referred to as gc1120) is provided in FIG. 4.

An enhancer element is present in a 2.2 kb fragment approximately 11.5–15 kb upstream from the qmf1 gene, in restriction fragment P3. The DNA sequence of fragment P3 is set forth hereinbelow as Sequence I.D. No. 3.

```
  1 ACGTTGTCAA GGAAAATTCT GAGTCTTTTT TAAAAGTGAA AGCCAACACA

51 GTAGCACTGA CACTTGTGTG TATTTGTGGT GAGGTCAATG ACTGTTATGG

101 ATTTTAGACT GTTTTTTTTC TGCCTGTGCC ATTCTGGCTA CCACCTCTGC

151 TCCTTGAAGT GACTCTGCTT TGCTTCTTTC TGTAATATAT CCCATCTGGA

201 CATGGTCCAA GTGGAAAGTG ACTCAAAACT AATCAAACCT CAGAAGGTCA

251 AAANTGAAAA GAGGTACAGT TCAGGGAAAT ACATGTTAGA ATACGTGTTA

301 GAGAAGTTGT GACTGGTGAT ATGAGCAGCT TGTAGCAAGG TCATGTTTTC

351 CCCTAACACT GCTTTGTGAG CACTTTGGAA AGCCTACTTT TGCTCAGGTT

401 TTGTCTGATG TGTCCCAGAA CGGGATCATC CATATTTCCT TGAAGGATGC

451 TTATGGTCTA GAATCTGGGA TGCAAACAGG ACTGAGGGAC ACATCTTGTG

501 AGGCAGCAGT AAGGCCATGG TACGTGGGCA GAGGGAGGGT AGTGAAGTTT

551 GCCATGTGTA GCTTTTGACT TGTAGCTGTN TGCTTTGAAG CAGGAGACAA

601 GAAGATTTAT TTTCCTTTTT GAAGGAAGAT CAGTGCACAG CAAAGATAGG

651 TGAGAAGTTC CAAGGAAAAC TAAACAGAGA AGAGAAGCAG CACTAACTGG

701 CAGAGTGGGC CAAACCTTTC ACTGTTGTAT ATGGGCATTA CTCATACAAC

751 TTCAAGAGAG TACATGATTC AACTGAGCAT GTACCAGCTG AGGGCCTGGC

801 CCATAATGTT CNTTATAAAG GTCCGATTCC TCCCCAAATA GTTTTTCCCT

851 CTCTCTTCAA AGGGGGCACCTGTTGTTGGAG GAGCTGGTGA TGATACTGGA
```

```
-continued
 901 TTAGTGCACA TGCGGTCAGC CCACTTGGCC TCGGCCCTTT GGACCCAAAA

951 TGAACTCCAG CTGCTGTTAC CCAGAGCAGG TGCTTCATCC AGCCTGTGCA

1001 GCTGTTTGAA TGCATGCTGT TGTGGCCAAT AGGCGGGGTG AGTCCTCTGA

1051 ACTACCAGGG GAAGAGCTGG TCAGCAGGAG GGAAGGGAAA GGCACAGAGC

1101 TGGGTTTCTT ATACCCAGCA TTTAGCAAGG AGACAGTGTT CCAGCATAGT

1151 ATGGTGGAAA TGGGAAACAG TGGCTGGTAT CCTGCATGCA ACATGCCCAC

1201 ATGACCCAGT GATGGATGCT TGTTCCCAAA ATGAGGCTGA GACCTATAGA

1251 ATACCAGCAG GACCCTGACA AATGCTGGAT CTGTAAGATG CTGAATCTCC

1301 CTTGTCAGTT ACTGGCCTAG TGTGAGACAT TCAGAGGGCT GCTGGCATCT

1351 AACAGTTACT CAGTGTTTTC AGCCACTGGT TTAAAGCTTT AAAGAGCTGC

1401 CTGGCGAAGG TGAGATAGGC GCAGAGCGCG TGCAGGGTGA ATATCTGTGA

1451 CGTGCAANAG CTGAAACCAG CAGCAAAGGA AGATGACAAA AGCAGAGGGA

1501 AATGGGTTAA GATGCAGCCA CGGGAGTGCA AGGGACTGTG CCAGGTCAGT

1551 GGAGGGTGAG GAGACNCGGG CGTTCAGAGT TAGGGAAGGC TGGAAGTCAG

1601 CAGCCAGAGT TTGAAGAAGG AGTATAGACA GGTAACACCA ATGGTAGAGC

1651 AGTGGTAACC CAGGGAGGGN NAGAGAGAAG GGAGCAGGGC AGGNNTGAAG

1701 GTTTCTTTTT TCTACATTGC ATATGGTTTC AGTCAGGTCT CATCAGCCAG

1751 GCTTCTCATT CTTCATGCCT TTGCTAATTG CTCAAGCAAG CTCTCAGCGA

1801 ACCTCCATAT TTCATTTTTC ATTACAGTGT GGCGCAAGCC CAGGAGAAAA

1851 ACATAAATAT TTGAGGCCTC TCTTTGTCAG GAAATGGGAT TTCNGCAGGT

1901 GCTCATTTGC AAATACTGTG CATGCTTCTG AGGCTTGGNA TANGGCATTG

1951 CTAAATCCTG ATTCAGGATG CAAGAATGTC TCGTGGCCTC TGCCATGTAA

2001 ACTGTTGTCC GCCCAAGTTT GGAAGTCAGC CCTCAGTGAT GGCACTAGAC

2051 AAGTATGGGT GAAATGAGCA GCTTGGCTTC AGCACTGAGC AAGACTTGTT

2101 AAACACTGTA AGTACAGATG GGCCAATTCA CAGTTTGAAT AGTATAACAA

2151 TACATATATA TATAATATTA TGGCTTTTTC TGCAGGNNNT CGANNNNANN

2201 NNNNNCGATA CCGACGACCT CGAGGGGGGC CGGTA
```

It is commonly expected that expression of a gene will be controlled at least in part by a promoter sequence situated immediately 5' to the transcription start site. However, some gene are additionally regulated by enhancer elements, which can be located at positions far removed from the gene itself. Such enhancer elements may be found far upstream from the gene (as much as 50–100 kb, in some instances), or downstream from the gene in the 3' untranslated region, or even within the gene itself, in an intron. Alternatively, a gene may be expressed without the control of any enhancer element. See S. D. Gillies et al., Cell 33: 717–728 (1983); E. Serfling et al., Trends in Genet. 1: 224–230 (1985).

In spite of the difficulty in predicting if, or where, an enhancer element may exist, once an enhancer sequence for a particular gene is identified, it is likely that a similarly situated enhancer element will also be presented in related genes, or homologous genes from other species. Thus, in accordance with the present invention, the above-described human myoD enhancer was discovered and characterized as a 1.7 kb fragment existing 18–22 kb upstream from the human myoD transcription start site. Once the human myoD enhancer had been discovered and located, according to methods described herein, the upstream region of the quail myoD gene (qmf1) was examined for the presence of a similarly situated enhancer element. Such an enhancer was identified, at approximately 15–17 kb upstream from the qmf1 transcription start site. Although this enhancer is of different sequence homology from the human myoD enhancer, and directs a somewhat different pattern of myogenic development in mouse embryos, it comprises the basic characteristics of the myoblast-specific enhancer element provided by the present invention.

Thus, both the human myoD gene and the quail qmf1 gene have been shown to possess upstream enhancers of gene expression. As described in the Background section, MyoD and the qmf proteins are part of the bHLH family of myogenic regulatory proteins. These proteins have been shown to possess a high degree of evolutionary conservation. Pownall et al., supra. For this reason, the presence of an upstream enhancer in both the human myoD gene and the qual qmf1 gene is a clear indication that such an enhancer element is also present in the other genes of the bHLH myogenic regulatory protein family. This is even further the case when it is observed that human myoD and quail qmf1 are not the most closely related members of the bHLH family.

In view of the relationship among the members of the BHLH myogenic regulatory protein family, this invention provides a transcription control element which comprises an upstream enhancer from any one of the bHLH family. The bHLH family includes, but is not limited to: (1) MRF4 (mouse, rat, human); (2) myog (chick, mouse, rat, human); (3) MyoD (human, sheep, mouse, Xenopus, Drosophila, sea urchin, C. elegans, quail (including qmf1, qmf2 and qmf3); (5) myogenin; and (6) myf5 (bovine, human, Xenopus). The methods set forth herein for analyzing the upstream region of any bHLH myogenic regulatory gene will be appropriate for identifying and locating such enhancer elements. Moreover, it will be apparent to one skilled in the art that the preferred way for identifying such an enhancer is through a functional assay, as described herein. For example, the two myoD enhancer elements specifically exemplified herein both possess the same basic functional characteristics of enhancing gene expression in non-myogenic or myogenic cultured cells, and specifically enhancing gene expression in non-cultured myoblasts, even though the respective enhancers do not exhibit sequence homology.

Myoblast-specific transcription control activity may be analyzed by preparing constructs in which the putative enhancer element is positioned upstream from a common reporter gene, such as the gene encoding chloramphenicol acetyltransferase (CAT). Methods for testing the promoter/enhancer activity of cloned DNA segments using the CAT reporter gene are described in greater detail in the examples below.

Once enhancer sequences have been identified, their myoblast-specificity may be tested in vivo by examining reporter gene expression in transgenic mouse embryos. The transcription control element is coupled to a reporter gene, such as the lacZ gene, and introduced into animal embryos by pronucleus injection, according to known methods. Reporter gene expression may be monitored by observing whole mounts and serially sectioned embryos several days (e.g., 11–12) post-coitum, the time at which myogenic cells of the somatic myotome limb buds first express myogenic gene transcripts at high concentration. If the putative transcription control element is indeed myoblast-specific, and active in myogenic cells, the reporter gene should be expressed under these conditions. Methods of testing potential myoblast-specific transcription control elements in vivo are described in greater detail in the examples below.

II. Methods of Using Myoblast-Specific Transcription Control Elements

A. Somatic Gene Therapy

The transcription control elements of the present invention may be used to considerable advantage in myoblast-mediated gene therapy. Because myoblasts proliferate and fuse together, they are capable of contributing progeny comprising recombinant genes to multiple, multinucleated myofibers in the course of normal muscular development. Dhawan et al., Science, 254: 1509–12 (1991). The transcription control element of the present invention may be used in conjunction with existing myoblast transfer techniques to provide high expression of recombinant genes, as well as great specificity of gene expression. It should be noted that a significant feature of the transcription control element of the present invention is that it is inactive after myoblasts have differentiated into mature muscle cells. Thus, such an element provides a needed control of gene expression, whereby recombinant genes may be expressed during myoblast proliferation of fusion, but will be "turned off" once the myoblast cells and their progeny have differentiated, or shortly thereafter. In a preferred embodiment, the transcription control element of the invention comprises an enhancer element that becomes inactive once myoblasts have differentiated into muscle cells, used in conjunction with a promoter element that is not myoblast-specific.

Myoblast transfer, using genetically engineered myoblasts according to the present invention, may be accomplished by methods known in the art. See, e.g., Dhawan et al., supra. For example, cultured myoblast cells may be genetically altered to comprise stably incorporated recombinant genes under myoblast-specific transcriptional control using transfection or infection methods known in the art. Such transfection or infection methods include transfection via mammalian expression vectors or high-efficiency retroviral-mediated infection. Myoblasts genetically altered in this way are then examined for expression of the recombinant gene. Such genetically altered cells are expanded for introduction into muscle tissue in vivo.

For injection of myoblasts into muscle, cells may be trypsinized, washed and suspended in, e.g., phosphate buffered saline (PBS). $10^6$–$10^7$ myoblasts may be delivered in a small volume (e.g., 10–100 microliters) in a series of several injections throughout the muscle tissue to be treated. The transferred recombinant myoblasts will express recombinant gene product during the period in which they proliferate and begin to fuse with existing muscle cells. However, once this period ends, the enhancer controlling the recombinant gene will be deactivated, whereupon recombinant gene expression ceases.

Myoblast transfer using a myoblast-specific enhancer of the present invention may be employed to particular advantage in manipulating autocrine regulation of muscle development (i.e., the ability of a myoblast to regulate its own growth). Genes encoding growth factors (e.g., FGF or insulin-like growth factors), placed under the control of a myoblast-specific enhancer of the invention, could be used to genetically alter myoblasts. These myoblasts could be transferred into muscle, where the recombinant genes would be expressed. The growth factors expressed by the recombinant myoblasts would enable the recombinant cells to proliferate as myoblasts to a greater extent than would a non-recombinant myoblast, thus expanding the population of myogenic cells in the muscle tissue being treated.

Constructs containing a potentially useful gene under the control of myoblast-specific transcription control elements of the invention may be tested in cultured cells prior to undertaking myoblast transfer into a living organism. For example, such a construct, placed in an appropriate expression vector, may be used to transfect 23A2 myoblasts, as described in greater detail in Example 2 below. The amount of recombinant protein expressed by the contruct may be measured according to standard methods (e.g., by immunoprecipitation). In this manner, it can be determined in vitro whether a potentially useful protein, encoded by a gene under the control of a transcription control element of the invention, is capable of expression to a suitable level that it will be appropriate for myoblast transfer.

Additionally, potentially useful constructs comprising recombinant genes under the control of transcription control elements of the invention may be tested in developing animal embryos. Testing of expression in embryonic animals may more closely approximate expression conditions in myoblasts used for myoblast transfer. Methods for introducing such constructs into mouse embryos are described in greater detail in Example 3 below.

B. Germline Genetic Manipulation

As mentioned earlier, recombinant genes under the control of transcription control elements of the present invention may be used for genetic alteration of embryonic cells to create transgenic animals with improved muscular characteristics. A recombinant gene under the control of a myoblast-specific transcription control element may be introduced by pronucleus injection, as described in Example 3 below. Instead of sacrificing the embryos, as described in the Example, the embryos may be implanted into a recipient female and the animals allowed to be born. Putative transgenic animals can be raised and then bred to determine if there has been inheritable incorporation of the recombinant gene into the animal's genome.

During embryological development of a transgenic animal, the recombinant gene should remain dormant until such time as myoblast determination begins. The recombinant gene should then become activated in the myoblasts, conferring the benefit of the selected recombinant gene product. For example, a gene encoding growth hormone may be placed under the control of the transcription control element of the invention, and become activated throughout the period of the animal's growth in which muscle formation is occurring. As muscle tissue matures, the transcription control element will become deactivated, as mentioned earlier, and the recombinant gene product will cease to be produced.

It should be noted in this regard that the mouse embryological system described hereinabove, and in Example 3 below, is an extremely useful animal model system for testing recombinant genes under the control of transcription control elements of the invention. These animals may be manipulated in the laboratory as embryos, and also raised to adulthood under controlled conditions. Thus, potentially useful recombinant genes may be screened for expression and effectiveness throughout the growth period of a mouse, and evaluated on that basis for efficacy in other animals.

The following examples are provided to describe the invention in further detail. These examples are intended to illustrate and not to limit the invention.

EXAMPLE 1

Isolation and Cloning of a Human myoD Transcription Control Element

The transcription control element that regulates expression of the human myoD gene was identified and cloned. A full-length mouse myoD cDNA (Pinney et al., Cell, 53: 781, 1988) was used to screen a pWE15 human genomic MboI cosmid library (Stratagene, La Jolla, Calif.). Approximately 400,000 colonies on 20 duplicate nitrocellulose filters were hybridized at moderate stringency (65° C. for prehybridization and hybridization, 55° C. for washes) with a $^{32}$P-labelled random-primed mouse MyoD1 cDNA.

This screen yielded 4 recombinants representing 3 unique overlapping clones that spanned a total of 40 kb. Sequence comparison with human MyoD cDNA identified the hybridizing species as myoD.

EcoR1 maps of the clones were generated by the indirect end-labelling method, as described by Wahl et al., Proc. Nat'l. Acad. Sci. (USA), 84: 2160 (1987). The organization of the cosmid clone used in subsequent analysis (chMD-13) includes approximately 25.5 kb of DNA upstream and 4 kb downstream of the myoD gene, as shown in FIG. 1A. The approximate sizes of the restriction fragments of chMD-13 are as follows: 1, 1.7 kb; 2, 1.9 kb; 3, 4.1 kb; 4, 0.45 kb; 5, 9.7 kb; 6, 0.65 kb; 7, 0.25 kb; 8, 3.9 kb; 9, 6.4 kb; 10, 2.8 kb.

EXAMPLE 2

Measurement of Transcription Control Activity of a myoD-Regulating Transcription Control Element in Cultured Myogenic Cells Transcriptional activity of the myoD transcription control element described in Example 1 was assayed in 23A2 myoblasts, myogenic cells derived from the multipotential 10T1/2 cell line by 5-azacytidine treatment. Konieczny et al., Cell, 38: 791 (1984). This was accomplished by constructing several clones wherein different regions of the flanking sequence of myoD were fused to the chloramphenicol acetyltransferase (CAT) reporter gens, then assaying for CAT activity after transient transfection into proliferative 23A2 myoblasts.

All cell lines were obtained from the American Type Culture Collection except 23A2, which was derived from 10T1/2 cells by 5-azacytidine treatment, as described above. C3H10T1/2 and 23A2 cells were maintained in Basal Medium Eagle (BME) medium supplemented with 15% fetal bovine serum (FBS). JEG-3 human choriocarcinoma cells were maintained in Dulbecco's modified Eagle medium (DMEM) supplemented with 10% FBS, HepG2 human hepatoma cells were maintained in 50:50 DMEM Ham's F12 supplemented with 10% FBS. All media was supplemented with penicillin G (100 U/ml) and streptomycin sulfate (100 µg/ml) (Gibco, Grand Island, N.Y.). All DNAs used in transfections were prepared by alkaline lysis and double banded in CsCl gradients, according to standard methods. Cells were transfected by the calcium phosphate precipitation method as follows. Cells were trypsinized and plated at $2\times10^5$ cells per 100-mm plate (10T1/2 and 23A2 cells) or passed ~1:10 from 50% confluent plates (JEG-3 and HepG2 cells). The following day cells were fed fresh medium, and 3 hours later calcium phosphate-DNA coprecipitates (1 ml per 100-mm dish) were added (0.8, pmole of test vector, brought to 25 µg with vector carrier DNA). About 16 to 18 hours later, the precipitates were removed, cells washed one time in basal medium without FBS, and then fed complete medium. After 48 hours, cells were harvested and lysed by freeze-thawing. CAT enzyme activity in cell extracts was quantified with the xylene extraction method, as described by Seed et al., Gene, 67: 271 (1988), with $^3$H-labeled chloramphenicol (31.2 Ci/mmole, New England Nuclear) and N-butyryl coenzyme A (Sigma, St. Louis, Mo.). Equivalent amounts of protein (15 to 25 µg as determined with a BioRad protein kit and bovine serum albumin as a standard) and a reaction time of 1 hour were used in all CAT assays, which kept all values within the linear range of the assay. In a typical experiment with 15 µg of protein, 1% conversion of $^3$H-labelled chloramphenicol to butyryl $^3$H-chloramphenicol was ~45,000 cpm as determined by scintillation counting.

The CAT constructs are shown in FIG. 2. The constructs were prepared by the following method. ptkCATΔEH, derived from pBLCAT2 (Luckow et al., Nuc. Acids Research, 15: 5490 (1987)), by deletion of the Nde 1-Hind III fragment of pUC 18, was used in all transfection experiments. Similar CAT activity vectors are also commercially available from, e.g., Promega Biotech (Madison, Wis.), and may be substituted for the vectors used herein. All cloning procedures were by standard methods. A 2.8 kb fragment containing the myoD promoter, derived from pBluescript II KS+ (a widely pUC derivative available from Promega Biotech) sequencing deletion, was generated by digestion with SacI followed by partial digestion with Kpn I (both sites derive from the multiple cloning site of the pBluescript vector) and was blunt-end-ligated into ptkCATΔEH after digestion with Xba I and Bgl II (thereby removing all HSVtk promoter sequences (from −105 to +51). The resulting construct contains ~2.7 kb of human sequences extending from an Eco R1 site ~2.5 kb 5' of the myoD gene (see FIG. 1A) to +198 relative to the TATA box (nucleotide −37 relative to the start of translation; see Sequence I.D. No. 1). The −24CAT construct was generated by digesting chMD-13 with NotI, followed by partial cleavage with EcoR1. Partial cleavage products were size-fractionated on a 0.6% agarose gel, and fragments of about 20 to 25 kb were gel purified and directionally cloned into −2.5CAT that had been digested with NotI and partially digested with EcoR1 (vector sequences in −2.5CAT contain two EcoR1 sites). The resulting clone contained continuous human sequences from the distal NotI site through +198. Fragments 2 through 8 were cloned into the Xba1 site of −2.5CAT by digesting chMD-13 with NotI and EcoR1, and blunt end-ligating fragments into the unique Xba1 site (see FIG. 2). Fragment 3 was cloned in both orientations upstream of the tk promoter by blunt-end-ligation into the unique BamH1 site (F3/tkCAT and F3'/tkCAT). The −24ΔF3CAT construct was generated by partially digesting −24CAT with EcoR1 ligating gel-purified, size-selecting digestion products, and screening by colony hybridization for clones missing only fragment 3.

As shown in FIG. 2, −2.5CAT and −24CAT refer to CAT reporter gene constructs with the minimal and maximal amounts of human myoD 5' sequences tested in transient transfection assays. These sequences in −2.5CAT extend from the EcoR1 site ~2.5 kb upstream of myoD to +198 relative to the TATA box (see Sequence ID No. 1). Fragments 2 through 8 of chMD-13 (see FIG. 1A) were tested for transcriptional enhancing activity after cloning into the XbaI site of −2.5CAT, as shown in FIG. 2.

Figure 3:
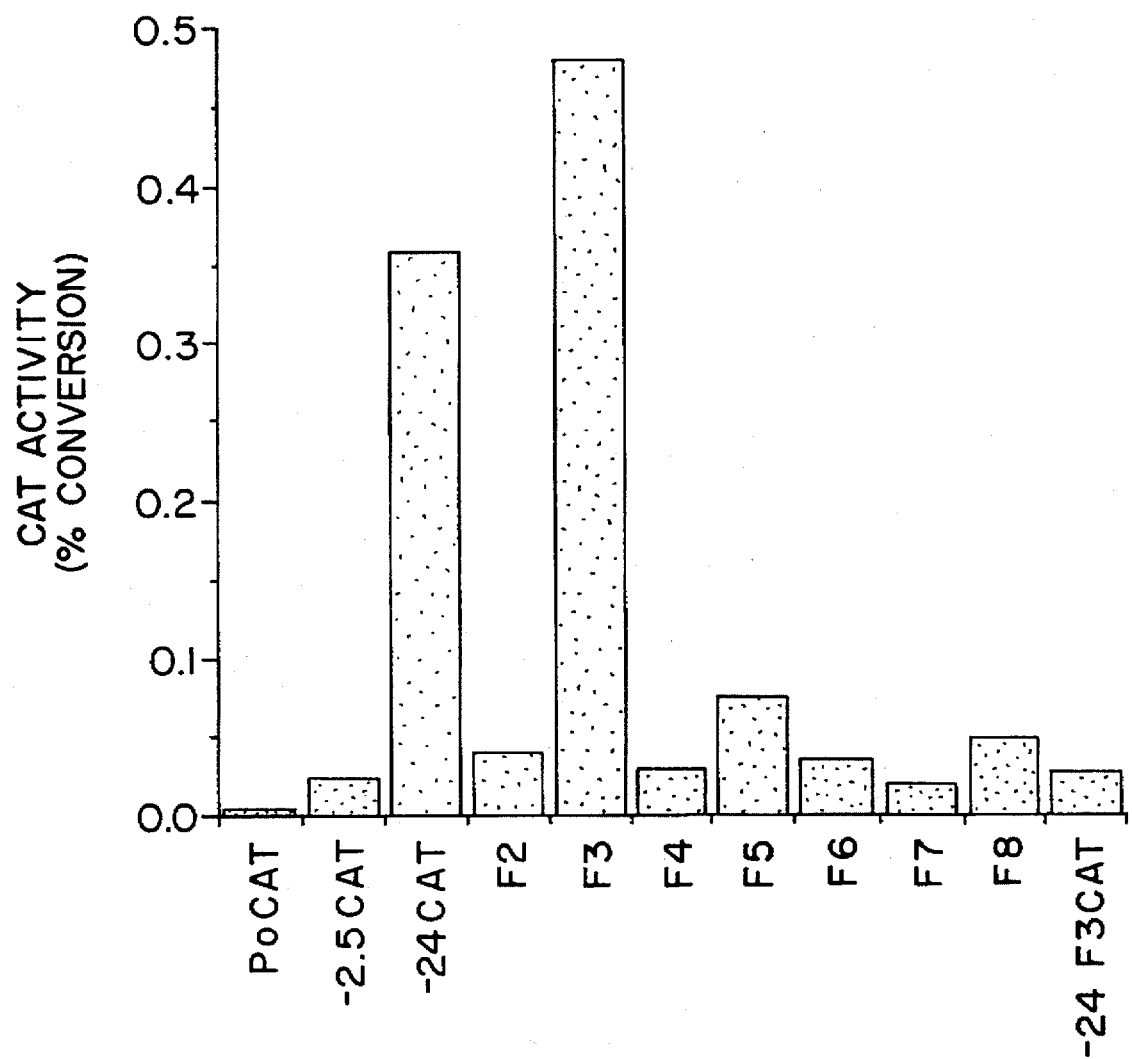
FIG. 3 shows transient transfection of 23A2 myoblasts with CAT reporter gene constructs containing 5' flanking sequences upstream of the human myoD gene. PoCAT is a promoterless CAT gene construct, and –24ΔF3CAT is identical to –24CAT except that Fragment 3 has been deleted. Y-axis: CAT activity represented as the percent conversion of $^3$H-chloramphenicol to butyryl-$^3$H-chloramphenicol per microgram of protein per hour at 37° C.

The results of transient transfection assays are shown in FIG. 3. It can be seen that the construct comprising the myoD promoter region (−2.5CAT; FIG. 2) yielded CAT activity 5–10 fold greater than a promoterless CAT construct (PoCAT). The −2.5CAT activity constituted ~20% of CAT activity achieved when another promoter, the herpes virus thimidine kinase (HSVtk) promoter is used (data not shown). Moreover, addition to −2.5CAT of fragments F2 or F4–F8 yielded no significant increase in CAT activity. However, when Fragment F3 was added to −2.5CAT, CAT activity was stimulated ~10 fold above the promoter alone. In fact, activity of that construct was even greater than activity of −24CAT, which comprises all of fragments F1–F8 (FIG. 2). The F3 fragment was shown to be critical for CAT expression through the construction of a CAT construct comprising F1–F8, but lacking F3 (−24ΔF3CAT). This construct stimulated CAT activity no better than the myoD promoter above (FIG. 3).

Thus, the myoD enhancing activity was quantitatively recovered in a fragment 18–22 kb 5' to myoD (Fragment 3, FIG. 1A). In addition to enhancing the activity of the myoD promoter, Fragment 3 was also found to enhance the activity of the HSVtk promoter, and was equally effective in both orientations. In addition, Fragment 3 in either orientation exhibited only background CAT activity in a promoterless CAT construct, demonstrating that Fragment 3 does not contain promoter activity.

Because myoD is expressed exclusively in skeletal muscle, the muscle specificity of the myoD transcription control element was investigated. The 10T1/2 cells are non-myogenic and do not express myoD, but are converted to myogenic cells by 5-azacytidine, by forced expression of the myogenic regulatory cDNAs, and by transfection of the genomic locus myd. The myoD promoter and enhancer, as well as the entire 24 kb of 5' flanking sequence, were as active in 10T1/2 cells as in 23A2 myoblasts. In stable transfection assays, these control elements also showed comparable activity in 10T1/2 and 23A2 cells.

A variety of cell lines were tested to determine whether multipotential 10T1/2 cells were unique among non-myogenic cells in their ability to express the myoD promoter and enhancer. These included Ltk- cells, three 10T1/2-derived adipocyte cell lines, BNL liver cells, HepG hepatoma cells and JEG-3 choriocarcinoma cells. The myoD enhancer and promoter were active in all of these cell lines except JEG-3 cells. Activity was relatively low in HepG2 cells, but in the other cells lines was comparable to that in 23A2 myoblasts. Similarly, the resident human myoD gene was activated when chromosome 11 was transferred from primary human fibroblasts to various tissue culture cell lines. Expression of the myoD enhancer and promoter in these non-myogenic cells, which do not express any known helix-loop-helix myogenic regulatory proteins, indicates that their activity is not dependent on auto- or cross-activation by members of the helix-loop-helix myogenic protein family.

EXAMPLE 3

In Vivo Myoblast Specificity of a myoD Transcription Control Element

Although the myoD transcription control element is active in non-myogenic cultured cells, it was found to be specific for myogenic cells in vivo. To determine this in vivo specificity, two lacZ reporter gene constructs were tested in transgenic mouse embryos.

The lacZ vector, pPD46.21 was used in transgene constructions. pPD46.21 is identical to pPD1.27 (Fire et al., Gene, 93: 189 (1990)) except that it lacks the sup-7 gene. It contains an initiation codon and SV40 T antigen nuclear localization signal just upstream from lacZ, and polyadenylation sequences from the SV40 early region downstream of lacZ. Similar lacZ reporter constructs are commercially available (e.g., Promega Biotech, Madison, Wis.) and may be substituted for the lacZ constructs used herein. The −2.5lacZ and F3'/−2.5lacZ vectors were constructed by digesting −2.5CAT and F3'/−2.5CAT at flanking SalI and XhoI sites and cloning gel-purified fragments into the SalI site in the 5' polylinker of pPD46 21 (thereby destroying the XhoI site). The −2.5lacZ and F3'/−2.5lacZ vectors yielded a faint or intense, nuclear localized signal, respectively, after transient transfection into 23A2 myoblasts (data not shown). DNAs for injection were digested with NotI to remove pUC19 sequences, and lacZ fusions were purified on agarose gels. Microinjections of the plasmid-free lacZ fusion genes into the pronuclei of fertilized eggs of the commercially available inbred strain FBV/N were performed according to standard methods. See, Hogan et al., *Manipulating the Mouse Embryo: A Laboratory Manual*, Cold Spring Harbor Laboratory, N.Y. (1986); M. Shani, Mol. Cell Biol., 6: 2624 (1986). Embryos 11.5 days postcoitum (p.c.) were stained for 30 to 60 min in 1% paraformaldehyde, 0.2% glutaraldehyde in 0.1M phosphate buffer, pH 7.4. After rinsing, embryos were stained for β-gal according to the method of Sanes et al., EMBO J., 5: 3133 (1986). Following photomicrography, the embryos were embedded in paraffin, serially sectioned at 8 μm, and sections were counterstained with nuclear fast red.

The promoter/lacZ construct (−2.5lacZ) contained 2.5 kb of human sequences 5' to the myoD gene cloned upstream of lacZ, whereas the other (F3'/−2.5lacZ, contained the 2.5 kb of flanking DNA as well as the upstream enhancer fragment cloned in an antisense orientation. The −2.5lacZ construct was introduced into nine embryos by pronucleus injection. Whole mount and serially sectioned embryos were analyzed for β-galactosidase (β-gal) activity at 11.5 days p.c., the time at which myogenic cells of the somitic myotome and limb buds first express myoD transcripts at high concentrations. None of the mouse embryos injected with −2.5lacZ showed lacZ expression in somites, limb buds, or any other populations of myogenic cells.

Four of fourteen embryos injected with F3'/−2.5lacZ contained lacZ-expressing cells. In all four embryos, this transgene was activated in cells from every skeletal muscle-forming region shown by in situ analyses to express the endogenous myoD gene. The most prominent feature of these embryos was the intense staining of the somites and limb buds. Somite staining yielded a metameric pattern of β-gal-positive cells along the central axis of the embryo. Observations of histological sections of three embryos demonstrated that somitic lacZ staining was confined to cells in the myotomal compartment of the somite. At 11.5 days p.c., lacZ-expressing cells were observed in the myotomes of only the 20 to 25 most rostral somites; lacZ expression was not detected in somites approximately at the level of, or caudal to, the hind limb. In later stage embryos all somites expressed the lacZ transgene. This clearly defined rostrocaudal gradient of lacZ expression, which corresponds to the gradient of transcript accumulation for myoD and the other myogenic regulatory factors, reflects the rostrocaudal sequence of somite formation and maturation. The lacZ transgene is likely activated in a ventral to dorsal sequence because lacZ-expressing cells are confined to the ventral myotome in less mature caudal somites, but are present throughout the ventra-dorsal myotomal axis in more mature anterior somites.

All four lacZ-positive embryos contained β-gal-expressing cells in the proximal region of both the fore- and hind-limb buds. These cells were localized to the dorsal and ventral premuscle masses, which give rise to the skeletal musculature of the limb. The fore limb contained large populations of cells that expressed the transgene, whereas the hind limb contained few lacZ-expressing cells. Because myoblasts of the developing limb buds are derived from the somite dermomyotome, the smaller population of lacZ-expressing cells in the hind-limb bud probably reflects the earlier developmental stage of the somites at the level of the hind limb compared to rostral somites at the level of the fore limb.

The lacZ-expressing cells were also observed in the visceral arches, evident in whole mounts as patches or anteroposterior arrays of stained cells. In histological sections, groups of stained cells were found in the mesenchyme of the visceral arches, organized in centrally and peripherally localized masses. Transcripts for myoD, myogenin, Myf-5 co-localize to these regions of the visceral arches, which is compared of cells that will contribute to pharyngeal and facial musculature. In addition, presumptive muscle of the developing diaphragm stains intensely for β-gal. The lacZ transgene was not expressed in smooth and cardiac muscle, muscle types that do not express myoD. A stable transgenic line carrying this lacZ transgene gave the same, skeletal muscle-specific pattern of lacZ expression. These transgenic data establish that the myoD enhancer and promoter, which together constitute the myoD transcription control element, are the DNA elements through which myoD expression is regulated.

EXAMPLE 4

Isolation and Cloning of a quail myoD (qmf1) transcription control element

The enhancer element that regulates expression of the quail qmf1 gene was identified and cloned. A qmf1DNA clone (gC1083) (de la Brousse et al., supra) was used to screen a genomic DNA library of partial Mbo1 restriction fragments of quail embryonic primary myofiber DNA, ligated into BamHI-digested lambda EMBL3 arms (Stratagene), and plated on bacterial strain LE392. A total of approximately 400,000 primary plaques were screened, and 2 positive clones that hybridized under high stringency conditions (65° C. for prehybridization and washes) to a genomic fragment containing only 5' upstream sequences of the qmf1 gene were isolated. One of these clones was found to be similar to the previously-mapped lambda Charon 4A clone (de la Brousse et al., supra) while the other was found to overlap with that clone only in the first Exon region of the qmf1 gene. Restriction mapping of this latter genomic clone, referred to as gC1120, indicated that it contained approximately 18 kb of 5' qmf1 upstream region. A restriction map of GC1120 is set forth in FIG. 4. The approximate sizes of the restriction fragments (in kb) of gC1120 are as follows: R1, 6.1; R2, 2.0; R3, 4.5; R4, 1.7; R5, 0.7; R6, 4.1; R7, 0.8; R8, 6.5; R9, 4.1; P1, 0.7; P2, 1.8; P3, 2.2; P4, 1.4.

EXAMPLE 5

Measurement of Transcriptional Control Activity of qmf1-Regulating Transcription Control Element in Cultured Myogenic Cells Transcriptional activity of the qmf1 upstream region described in Example 4 was assayed according to the methods set forth in Example 1, except that quail primary myoblasts were utilized for transfection by qmf1-CAT reporter gene constructs instead of 23A2 myoblasts and a qmf1 promoter was used.

Figure 4:
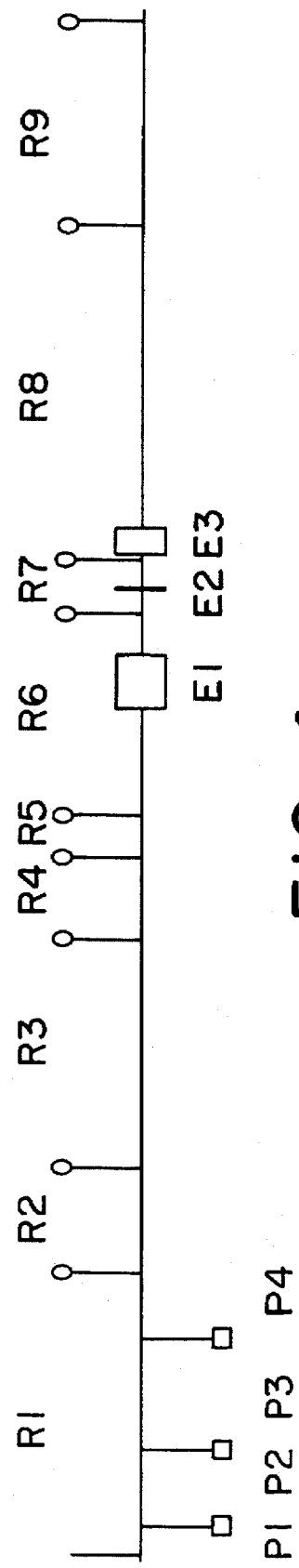
FIG. 4 is a map of λ EMBL3 clone gc1120, comprising the qmf1 (QmyoD) DNA locus from quail. EcoR1 (0) and Pst1 (□) restriction sites are indicated. Exons (E1, E2 and E3) of qmf1 are indicated. For reference, restriction fragments for enzymes shown are labelled sequentially from the 5' to the 3' end of the cloning vector (EcoRI fragments= R1–R9, PstI fragments=P1–P4).

For the CAT constructs, the CAT gene linked to the herpes virus TK promoter (pTKCATΔEH) was linked to each of the qmf1 restriction fragments shown in FIG. 4. Transcription enhancer activities of each restriction fragment was tested by measuring the CAT activities of cell extracts reported as percent conversion of $^3$H-chloramphenicol to butyryl-$^3$H-chloramphenicol per 10 μg protein per hour at 37° C.

Figure 5:
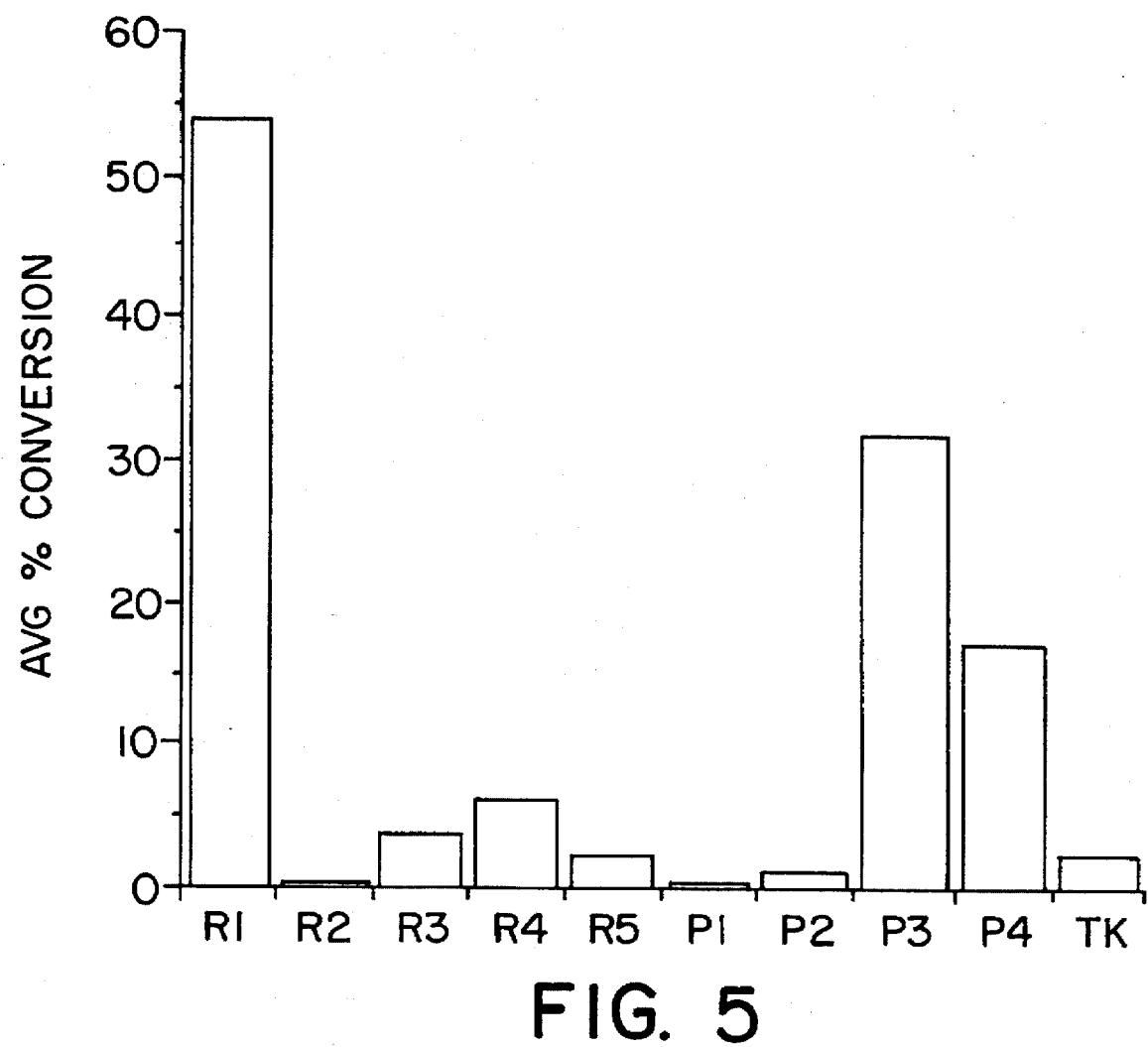
FIG. 5 shows transient transfection of quail primary myoblasts with CAT reporter gene constructs containing 5' flanking sequences upstream of the qmf1 gene. The CAT reporter gene was linked to the thymidine kinase (TK) promoter (pTKCatΔEH) and to the qmf1 restriction fragments shown in FIG. 4. On the x-axis, TK=thymidine kinase promoter alone; R1–R5 and P1–P4=thymidine kinase promoter combined with the restriction fragment indicated. Y-axis: CAT activity represented as the percent conversion of $^3$H-chloramphenicol to butyrl-$^3$H-chloramphenicol per 10 μg protein per hour at 37° C.

The results of the transient transfection assays are shown in FIG. 5. It can be seen that the construct comprising the R1 or the P3 restriction fragments yielded the greatest CAT activity, 12–20 times greater than the CAT gene linked to the TK promoter alone. As can be seen from FIG. 2, the R1 region approximately 11.5–15 kb upstream from the qmf1 gene, in which is located the 2.2 kb sequence identified herein as Sequence I.D. No. 3.

EXAMPLE 6

In Vivo Myoblast Specificity of a Quail MyoD (qmf1) Transcription Control Element To determine the in vivo specificity of the qmf1 enhancer, a lacZ reporter gene construct comprising the aforementioned P3 restriction fragment was tested in transgenic mouse embryos, according to methods described in Example 3. The P3 lacZ plasmid for use in transgenic mice was constructed by first cloning a 2.4 kb SalI/XbaI fragments containing the qmf1 promoter into the SalI/XbaI sites of PD46.21. The 2.2 kb P3 fragment was then cloned into a PstI site adjacent to the qmf1 promoter to yield the final P3-qmf1-lacZ construct. This construct was utilized as described in Example 3.

The qmf1 enhancer was found to control lacZ expression in transgenic mouse embryos in a manner similar to, but not exactly like, that observed for the human myoD enhancer described in Example 3. The qmf1 enhancer was found to direct expression of the lacZ reporter gene in the myotome of the rostral somites by day 9 in transgenic embryos, whereas the human myoD enhancer directed expression later in myotomes (i.e., by Day 10–10.5). The qmf1 enhancer was expressed in the limb buds by Day 12.5, which is later than the human myoD enhancer, expressed at Day 10–10.5. The earlier expression of qmf1 in somite is localized to the central myotomal cell, and activation proceeds in a rostral-caudal progression. The later activation of the human myoD-enhancer-controlled lacZ occurs first at the level of the forelimb bud with prominent staining in the ventral regions of somites. Subsequent expression occurs in more anterior somites, which exhibit more dorsal activation than in the remaining somites. In contrast to the qmf1-enhanced lacZ, the human enhancer was found not to direct expression predominantly to the central myotomal muscles. Thus, the qmf1 and human myoD enhancers possess different developmental timing of expression in the somites and limb, and different spatial expression in the somites. These differences in spatial expression likely reflects the formation of different lineages of myogenic cells that give rise to different muscles of the embryo. However, both qmf1 and human myoD expression is restricted to the early embryonic myogenic lineages of the somite.

While certain aspects of the present invention have been described and exemplified above as preferred embodiments, various other embodiments should be apparent to those skilled in the art from the foregoing disclosure. The present invention, therefore, is not limited to the embodiments specifically described and exemplified above, but is capable of variation and modification without departure of the scope of the appended claims.

---

What is claimed is:

1. A DNA segment isolated from the region 10–30 kb 5' of the coding region of the human myoD gene having an enhancer activity in non-differentiated cultured skeletal muscle cells and in non-cultured skeletal myogenic cells, wherein said enhancer activity causes increased expression of a target gene when said DNA segment and said target gene are disposed within a DNA strand and said DNA segment is so positioned in the 5' direction relative to said target gene to permit said increased expression of said target gene.

2. The isolated DNA segment according to claim 1, positioned within 100 kilobases (kb) in the 5' direction of said target gene.

3. The isolated DNA segment according to claim 2, positioned between 10 kb and 30 kb in the 5' direction of said target gene.

4. The isolated DNA segment according to claim 1, isolated from a region approximately 18–22 kb in the 5' direction from said human myoD gene.

5. An anti-sense oligonucleotide having a sequence that hybridizes with the DNA segment according to claim 1.

6. A vector comprising the DNA segment according to claim 1.

7. A procaryotic or eucaryotic host cell transformed or transfected with the vector according to claim 6.

8. An isolated quail qmf1 DNA segment having an enhancer activity in cultured skeletal muscle cells and in non-cultured, skeletal myogenic cells, wherein said enhancer activity causes increased expression of a target gene when said DNA segment and said target gene are disposed within a DNA strand and said DNA segment is so positioned in the 5' direction relative to said target gene to permit said increased expression of said target gene.

9. The isolated DNA segment according to claim 8, isolated from a region approximately 11.5–15 kb in the 5' direction from said qmf1 gene.

10. A DNA segment isolated and purified from an approximately 25.5-kb fragment adjacent in the 5' direction to a human myoD gene, having a nucleotide sequence substantially the same as Sequence I.D. No. 2, described herein.

11. A vector comprising the DNA segment according to claim 10.

12. The DNA segment according to claim 10, consisting essentially of a nucleotide sequence substantially the same as bases 1–258 of Sequence I.D. No. 2, described herein.

13. The DNA segment according to claim 10, consisting essentially of a nucleotide sequence substantially the same as bases 1185–1757 of Sequence I.D. No. 2, described herein.

14. A DNA segment isolated and purified from an approximately 18-kb fragment adjacent in the 5' direction to a quail qmf1 gene, having a nucleotide sequence substantially the same as Sequence I.D. No. 3, described herein.

15. A vector comprising the DNA segment according to claim 14.

16. An isolated DNA segment having an enhancer activity in cultured cells, wherein said enhancer activity causes increased expression of a target gene when said DNA segment and said target gene are disposed within a DNA strand and said DNA segment is so positioned in the 5' direction relative to said target gene to permit said increased expression of said target gene, said DNA segment being isolated by a method comprising:

a) obtaining at least one test segment comprising DNA sequences disposed in the 5' direction 10–100 kb of a gene encoding a bHLH myogenic regulatory protein, one or more of said at least one test segment being suspected of having said enhancer activity;

b) preparing a set of test constructs, each said test construct comprising one said test segment, a reporter gene and a vector adapted for expression in a cultured eucaryotic cell, said test segment and said reporter gene being so located relative to each other and to regulatory sequences of said vector to permit expression of said reporter gene, as well as said enhancing activity, if present, of said test segment;

c) preparing a control construct comprising a reporter gene and a vector adapted for expression in a cultured eucaryotic cell, said reporter gene being so located relative to regulatory sequences of said vector to permit expression of said reporter gene;

d) introducing each said test construct or said control construct into cultured eucaryotic cells under conditions permitting expression of said reporter gene, said expression causing formation of a detectable product in an amount correlatable to said expression;

e) establishing a ratio of said amount of detectable product formed in said cultured eucaryotic cells comprising said test construct to said amount of detectable product formed in said cultured eucaryotic cells comprising said control construct, the magnitude of said ratio being indicative of said enhancer activity suspected of being possessed by said test segment; and f) identifying each said test segment possessing said enhancer activity, thereby isolating said DNA segment having said enhancer activity.

17. An isolated DNA segment having an enhancer activity specifically in myogenic cells of a living animal, wherein said enhancer activity causes increased expression of a target gene when said DNA segment and said target gene are disposed within a DNA strand and said DNA segment is so positioned in the 5' direction relative to said target gene to permit said increased expression of said target gene, said DNA segment being isolated by a method comprising:

a) obtaining at least one test segment comprising DNA sequences disposed in the 5' direction within 100 kb of a gene encoding a bHLH myogenic regulatory protein, one or more of said at least one test segment being suspected of having said enhancer activity;

b) preparing a set of test constructs, each said test construct comprising one said test segment, a reporter gene and regulatory sequences necessary for expression of said reporter gene in cells of a vertebrate embryo, said test segment and said reporter gene being so located relative to each other an to said regulatory sequences to permit expression of said reporter gene, as well as said enhancing activity, if present, of said test segment;

c) introducing each said test construct into cells of said vertebrate embryo under conditions permitting expression of said reporter gene, said expression causing formation of a detectable product in an amount correlatable to said expression;

d) determining which, if any, cells of said vertebrate embryo form said detectable product, the formation of said detectable product specifically in myogenic cells of said vertebrate embryo being indicative of said enhancer activity; and e) identifying each said test segment possessing said enhancer activity, thereby isolating said DNA segment having said enhancer activity.

* * * * *